(12) United States Patent
Umek et al.

(10) Patent No.: US 8,815,577 B2
(45) Date of Patent: Aug. 26, 2014

(54) ASSAY ELECTRODE HAVING IMMOBILIZED LIPID/PROTEIN LAYERS, METHODS OF MAKING THE SAME AND METHODS OF USING THE SAME FOR LUMINESCENCE TEST MEASUREMENTS

(75) Inventors: Robert M. Umek, Silver Spring, MD (US); Paula Denney Eason, Germantown, MD (US); Gargi Maheshwari, North Wales, PA (US); Anu Mathew, Gaithersburg, MD (US); Douglas Woods, Gaithersburg, MD (US)

(73) Assignee: Meso Scale Technologies, LLC, Rockville, MD (US)

( * ) Notice: Subject to any disclaimer, the term of this patent is extended or adjusted under 35 U.S.C. 154(b) by 0 days.

(21) Appl. No.: 10/208,526

(22) Filed: Jul. 30, 2002

(65) Prior Publication Data

US 2003/0124572 A1    Jul. 3, 2003

Related U.S. Application Data

(60) Provisional application No. 60/308,762, filed on Jul. 30, 2001.

(51) Int. Cl.
*C12M 1/34* (2006.01)
(52) U.S. Cl.
USPC .............. 435/288.7; 435/283.1; 435/287.1
(58) Field of Classification Search
USPC ............ 435/4, 6, 7.1, 7.9, 7.92, 287.2, 283.1, 435/288.7, 287.1; 422/68.1, 82.01; 436/164, 172, 518, 524, 528, 532
See application file for complete search history.

(56) References Cited

U.S. PATENT DOCUMENTS

| | | | | |
|---|---|---|---|---|
| 4,024,235 | A | * | 5/1977 | Weetall et al. ................ 435/5 |
| 5,147,806 | A | * | 9/1992 | Kamin et al. ................ 436/149 |
| 5,165,909 | A | | 11/1992 | Tennent et al. |
| 5,200,051 | A | | 4/1993 | Cozzette et al. |
| 5,240,863 | A | | 8/1993 | Shibue et al. |
| 5,308,754 | A | | 5/1994 | Kankare et al. |
| 5,597,910 | A | | 1/1997 | Gudibandle et al. |
| 5,637,201 | A | | 6/1997 | Raguse et al. |
| 5,641,623 | A | | 6/1997 | Martin et al. |
| 5,652,342 | A | * | 7/1997 | Zimmerman et al. ........ 530/403 |

(Continued)

FOREIGN PATENT DOCUMENTS

| | | | | |
|---|---|---|---|---|
| EP | 0522677 | * | 11/1992 | ............ G01N 21/76 |
| WO | WO 98 12539 | | 3/1998 | |

(Continued)

OTHER PUBLICATIONS

Yokoyama, K et al., *Biochimica et Biophysica Acta*, 538 (1978) 384-396.

(Continued)

*Primary Examiner* — Melanie Y Brown
(74) *Attorney, Agent, or Firm* — Scully, Scott, Murphy & Presser, P.C.

(57) ABSTRACT

Improved systems, system components, and methods for performing assays involving biological membranes and/or components thereof. Preferred luminescence test measurements are conducted using an assay module with integrated electrodes having biological membranes and/or components thereof immobilized thereon with a reader apparatus adapted to receive assay modules, induce luminescence, preferably electrode induced luminescence, in the wells or assay regions of the assay modules and measure the induced luminescence.

53 Claims, 14 Drawing Sheets

(56) References Cited

U.S. PATENT DOCUMENTS

| | | | |
|---|---|---|---|
| 5,766,960 A | 6/1998 | Cornell et al. | |
| 5,851,531 A * | 12/1998 | Lazarus | 424/758 |
| 5,866,434 A * | 2/1999 | Massey et al. | 436/526 |
| 5,919,576 A * | 7/1999 | Hui et al. | 428/545 |
| 6,066,448 A * | 5/2000 | Wohlstadter et al. | 435/6 |
| 6,083,763 A * | 7/2000 | Balch | 506/9 |
| 6,136,268 A | 10/2000 | Ala-Kleme et al. | |
| 6,165,710 A | 12/2000 | Robinson | |
| 6,207,369 B1 | 3/2001 | Wohlstader et al. | |
| 6,214,552 B1 * | 4/2001 | Heroux et al. | 435/6 |
| 6,271,041 B1 * | 8/2001 | Leland et al. | 436/172 |
| 6,319,468 B1 | 11/2001 | Sheppard, Jr. et al. | |
| 6,319,670 B1 * | 11/2001 | Sigal et al. | 435/6 |
| 6,325,973 B1 | 12/2001 | Leland et al. | |
| 6,342,359 B1 * | 1/2002 | Lee et al. | 435/6 |
| 6,702,986 B1 * | 3/2004 | Leland et al. | 422/52 |
| 6,977,722 B2 * | 12/2005 | Wohlstadter et al. | 356/246 |
| 7,129,036 B1 * | 10/2006 | Van Acker et al. | 435/4 |

FOREIGN PATENT DOCUMENTS

| | | |
|---|---|---|
| WO | WO 99 51984 | 10/1999 |
| WO | WO 99 58962 | 11/1999 |
| WO | WO 99 63347 | 12/1999 |
| WO | WO 01/04626 | 1/2001 |
| WO | WO 02/074983 | 9/2002 |

OTHER PUBLICATIONS

Katagiri, Y. et al., *Carbohydrate Research*, 120 (1983) 283-292.
Ohno, S. et al., *Int. J. Immunopharmac.*, 16(9) (1994) 761-768.
Nagata, Y. and Burger, M.M., *J Biol Chemistry*, 249(10) (1974) 3116-22.
Lund-Johansen, F., Frey, T., Ledbetter, J.A. and Thompson, P.A., *Cytometry*, 25(2) (1996) 182-90.
Yang, Y-k. et al., *J Biol Chemistry*, 272(37) (1997) 23000-10.
Maswoawe, B et al., "The PerkinElmer ViewLux™ Imaging System and Image FlashPlate® Applications", PerkinElmer Life Sciences, Inc., 2002.
Proximity News, (1996), Issue No. 25.
The description of WGA coated Flashplates at http://lifesciences.perkinelmer.com/imageflashplate/ available as of Oct. 21, 2002.
The description of WGA coated SPA beads at http://www4.amershambiosciences.com/aptrix/upp00919.nsf/Content/DrugScr+SPA+Introduction%5CDrugScr+SPA+Modalities available as of Oct. 21, 2002.

\* cited by examiner

ASSAY ELECTRODE HAVING IMMOBILIZED LIPID/PROTEIN LAYERS, METHODS OF MAKING THE SAME AND METHODS OF USING THE SAME FOR LUMINESCENCE TEST MEASUREMENTS

CROSS REFERENCE TO RELATED APPLICATIONS

The present application claims benefit of U.S. Provisional Application No. 60/308,762 filed on Jul. 30, 2001, the entire contents of which are incorporated herein by reference.

1. FIELD OF THE INVENTION

This application relates to reagents, apparatus, systems, kits and methods for conducting chemical, biochemical and/or biological assays.

2. BACKGROUND OF THE INVENTION

Biological membranes play a multi-faceted role in cell biology. In addition to providing the physical barrier that defines a cell or organelle, biological membranes play a role in the cellular processes including the transport of nutrients and waste products, the maintenance of homeostasis within a cell or organelle, intercellular and intracellular signaling, environmental sensing, cellular reproduction, and cellular motility. Assays for components or activities associated with a biological membrane are used both to identify and measure particular types of cells (e.g., in cell typing, cell counting, and assays for pathogens such as bacteria and virus particles) and in basic biological studies of membrane function. The importance of membrane-associated proteins, lipids and sugars in cellular signaling has also made them important targets for the screening of drugs that affect signaling pathways.

Drug screening assays are often carried out using highly purified membrane-free preparations. For example, screens for inhibitors of a membrane receptor-ligand binding interaction often involve the use of purified detergent-solubilized membrane receptor proteins (or, alternatively, truncated membrane receptor proteins missing their trans-membrane domains). There is a trend, however, towards conducting assays using membrane components in their native state (i.e., assays employing tissue, whole cells or organelles, natural membrane fragments or vesicles, or membrane components reconstituted into synthetic membranes). Assays conducted using these types of complex reagents have several advantages including: i) membrane components are more likely to have their in vivo characteristics when associated with a membrane; ii) the use of membrane-bound reagents facilitates the monitoring of interactions involving more than one membrane-associated component; and iii) the use of membrane-bound reagents facilitates the study of membrane-bound activities (e.g., the measurement of down stream signaling events controlled by a membrane-associated receptor).

At this time, there are a number of commercially available instruments that utilize electrochemiluminescence (ECL) for analytical measurements including drug screening. Species that can be induced to emit ECL (ECL-active species) have been used as ECL labels. Examples of ECL labels include: i) organometallic compounds where the metal is from, for example, the noble metals of group VIII, including Ru-containing and Os-containing organometallic compounds such as the tris-bipyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485, herein incorporated by reference), oxalate, and persulfate for ECL from RuBpy and hydrogen peroxide for ECL from luminol (see, e.g., U.S. Pat. No. 5,240,863, herein incorporated by reference). The light generated by ECL labels can be used as a reporter signal in diagnostic procedures (Bard et al., U.S. Pat. No. 5,238,808, herein incorporated by reference). For instance, an ECL label can be covalently coupled to a binding agent such as an antibody, nucleic acid probe, receptor or ligand; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants, herein incorporated by reference). For more background on ECL, ECL labels, ECL assays and instrumentation for conducting ECL assays see U.S. Pat. Nos. 5,093,268; 5,147,806; 5,324,457; 5,591,581; 5,597,910; 5,641,623; 5,643,713; 5,679,519; 5,705,402; 5,846,485; 5,866,434; 5,786,141; 5,731,147; 6,066,448; 6,136,268; 5,776,672; 5,308,754; 5,240,863; 6,207,369 and 5,589,136 and Published PCT Nos. WO99/63347; WO00/03233; WO99/58962; WO99/32662; WO99/14599; WO98/12539; WO97/36931 and WO98/57154, each of which are herein incorporated by reference.

Commercially available ECL instruments have demonstrated exceptional performance. They have become widely used for reasons including their excellent sensitivity, dynamic range, precision, and tolerance of complex sample matrices. The commercially available instrumentation uses flow cell-based designs with permanent reusable flow cells. Recently, ECL instrumentation has been disclosed that uses reagents immobilized on the electrode used to induce ECL (see, e.g., U.S. Pat. No. 6,207,369 and Published PCT Application No. WO98/12539). Multi-well plates having integrated electrodes suitable for such ECL measurements have also been recently disclosed (see, e.g., copending Provisional Application No. 60/301,932 (entitled "Assay Plates, Reader Systems and Methods for Luminescence Test Measurements", filed on Jun. 29, 2001, hereby incorporated by reference).

The use of multi-well assay plates allows for the parallel processing and analysis of multiple samples distributed in multiple wells of a plate. Typically, samples and reagents are stored, processed and/or analyzed in multi-well assay plates (also known as microplates or microtiter plates). Multi-well assay plates can take a variety of forms, sizes and shapes. For convenience, some standards have appeared for some instrumentation used to process samples for high throughput assays. Assays carried out in standardized plate formats can take advantage of readily available equipment for storing and moving these plates as well as readily available equipment for rapidly dispensing liquids in and out of the plates. Some well established multi-well plate formats include those found on 96-well plates (12×8 array of wells), 384-well plates (24×16 array of wells) and 1536-well plate (48×32 array of well). The Society for Biomolecular Screening has published recommended microplate specifications for a variety of plate formats, the recommended specifications hereby incorporated by reference.

3. SUMMARY OF THE INVENTION

Accordingly, the present invention includes improved systems, system components, and methods for performing assays involving biological membranes and/or components thereof. Preferably, such systems and methods would be compatible with assay formats conducted in multi-well plates. Preferably, such systems, system components and methods would include and/or allow assay measurements to be conducted using electrode induced luminescence measurements (most preferably, electrochemiluminescence measurements). The invention thereby facilitates the application of electrochemiluminescence detection and its unique advantages to assays conducted on complex biological systems such as biological membranes, cells or tissues.

The present invention also relates to solid phase supports (preferably, electrodes) having biological membranes, membrane proteins and/or lipid/protein layers (and/or components thereof) immobilized thereon and methods of making and using the same. The invention also relates to assay modules comprising such electrodes (preferably assay plates, more preferably multi-well assay plates). Preferred embodiments include immobilized biological membranes, membrane proteins, or lipid/protein layers (and/or components thereof) that are comprised in or derived from, e.g., tissue, whole cells, virions, organelles, subcellular structures, membrane ghosts, membrane vesicles, membrane fragments, artificial lipid membranes, liposomes, etc. These immobilized assay components are, preferably, i) stable to assay conditions and storage; ii) tolerant to the presence of detergents (preferably, non-ionic detergents), proteins and/or complex biological matrices; iii) tolerant to immobilization, drying and rehydration; iv) useful in high-throughput screening techniques (most preferably, in a multi-well plate format); v) useful in electrode-induced luminescence measurements (preferably electrochemiluminescence measurements); and/or vi) capable of being prepared using simple, scalable, procedures. The invention also includes preferred methods for the biomaterial immobilization. These methods utilize direct passive immobilization, or mediated immobilization using lectins, or antibodies.

The assays of the invention are preferably coupled to a detection step that involves the use of an electrode, the generation of light, and the measurement of the generated light. Examples of processes that may be used in such a detection step include electrochemiluminescence (also referred to as electrogenerated chemiluminescence), electroluminescence, and chemiluminescence triggered by an electrochemically generated species. For the purposes of the application and for convenience, these three processes will be referred to as "electrode induced luminescence". Electrochemiluminescence involves electrogenerated species and the emission of light. For example, electrochemiluminescence may involve luminescence generated by a process in which one or more reactants are generated electrochemically and undergo one or more chemical reactions to produce species that emits light, preferably repeatedly. The invention also relates to assays and measurements that do not require the use of an electrode, for example, the assays of the invention may be based on measurements of chemiluminescence, fluorescence, bioluminescence, phosphorescence, optical density and processes that involve the emission of light from a scintillant. The invention also relates to assays and measurements that do not involve luminescence, for example, the assays of the invention may be based on measurements of electrochemical processes (e.g., processes involving the measurement or generation of current or voltage) or electrical processes (e.g., processes involving the measurement of resistance or impedance).

Using the invention, electrode-induced luminescence assays may be performed involving complex biological systems (e.g., tissue, whole cells, virions, organelles, subcellular structures, biological membranes, membrane ghosts, membrane vesicles, membrane fragments, artificial lipid membranes, liposomes, etc.), membrane proteins and/or lipid/protein layers, these elements being captured and/or immobilized on a solid phase support, preferably an electrode, more preferably an electrode in a multi-well plate or assay modules having a plurality of assay domains. These immobilized biomaterials may be used in a variety of applications including, but not limited to: i) the measurement of the complex biological systems and/or lipid/protein layers themselves or components therein; ii) the measurement of activities of the complex biological systems and/or lipid/protein layers; iii) the measurements of analytes that interact with the complex biological systems and/or lipid/protein layers and iv) the measurement of analytes that affect an activity of the complex biological systems and/or lipid/protein layers.

Surprisingly, the immobilization of biological membranes on electrodes (preferably carbon electrodes, most preferably carbon ink electrodes) results in stable lipid/protein layers that retain much of their biological activity (one of ordinary skill in the art would have expected most electrode surfaces, particularly carbon surfaces, to have a denaturing and/or disrupting effect on biological membranes and their components). Alternatively, the present invention provides methods for mediated immobilization of biological membranes and describes components necessary for mediated immobilization. In addition, the usefulness of these coated electrode surfaces in electrode induced luminescence assays (e.g., in electrochemiluminescence assays) is surprising since one of ordinary skill in the art would expect the presence of a lipid/protein layer on an electrode surface to significantly degrade its ability to carry out electron transfer reactions.

4. DESCRIPTION OF THE FIGURES

Figure 6:
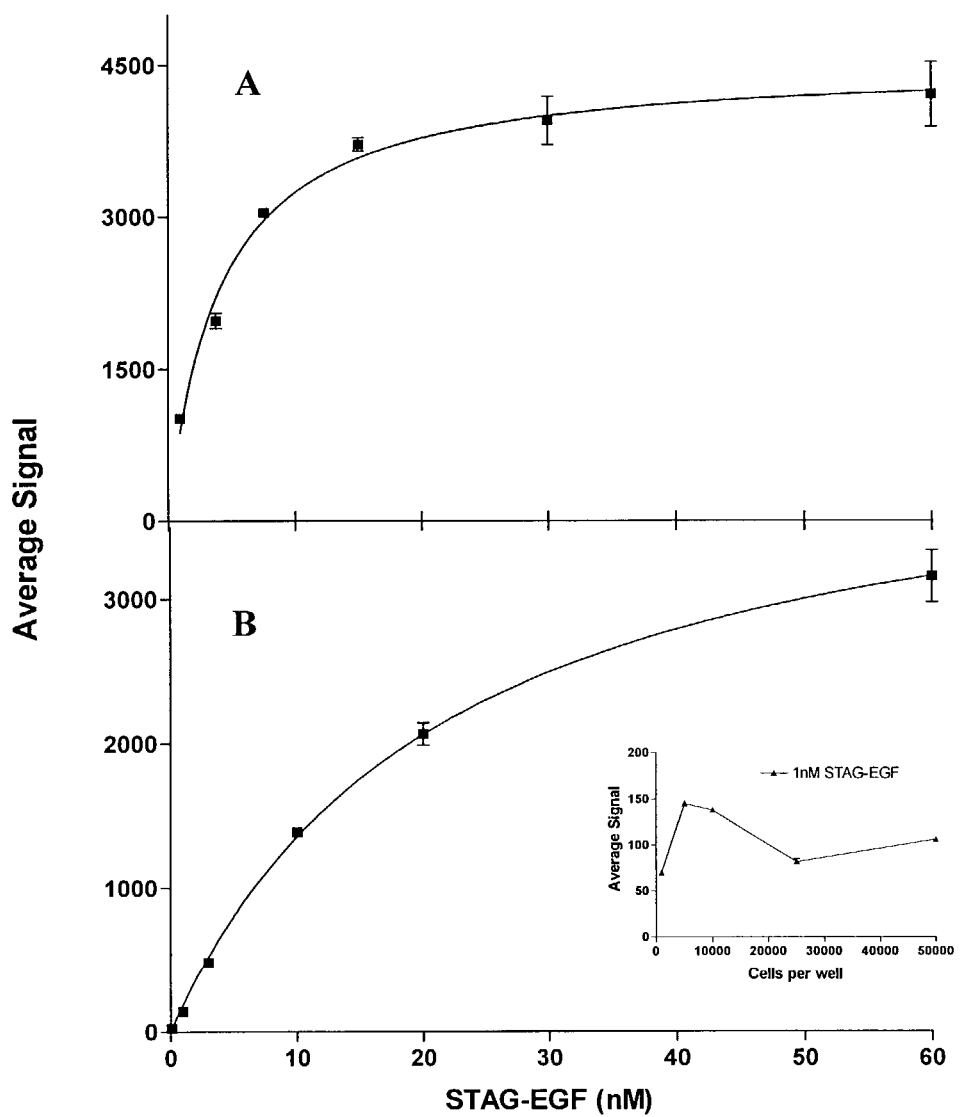
FIG. 6A shows the results of an electrochemiluminescence assay for binding of STAG-EGF to EGFR where the capture of EGFR containing membranes was mediated by anti-EGFR mouse antibody adsorbed on the electrode surface. The plot shows average ECL signal (vertical axis) as a function of the concentration of STAG-EGF (nM) (horizontal axis).

FIG. 6B shows the results of an electrochemiluminescence assay for binding of STAG-EGF to EGFR according to another embodiment of the invention where the whole EGFR-expressing cells were immobilized on the electrode surface. The plot shows average ECL signal (vertical axis) as a function of the concentration of STAG-EGF (nM) (horizontal axis). The insert FIG. 6A shows average ECL signal (vertical axis) as a function of the cell concentration of STAG-EGF (cell/well) (horizontal axis).

Figure 7:
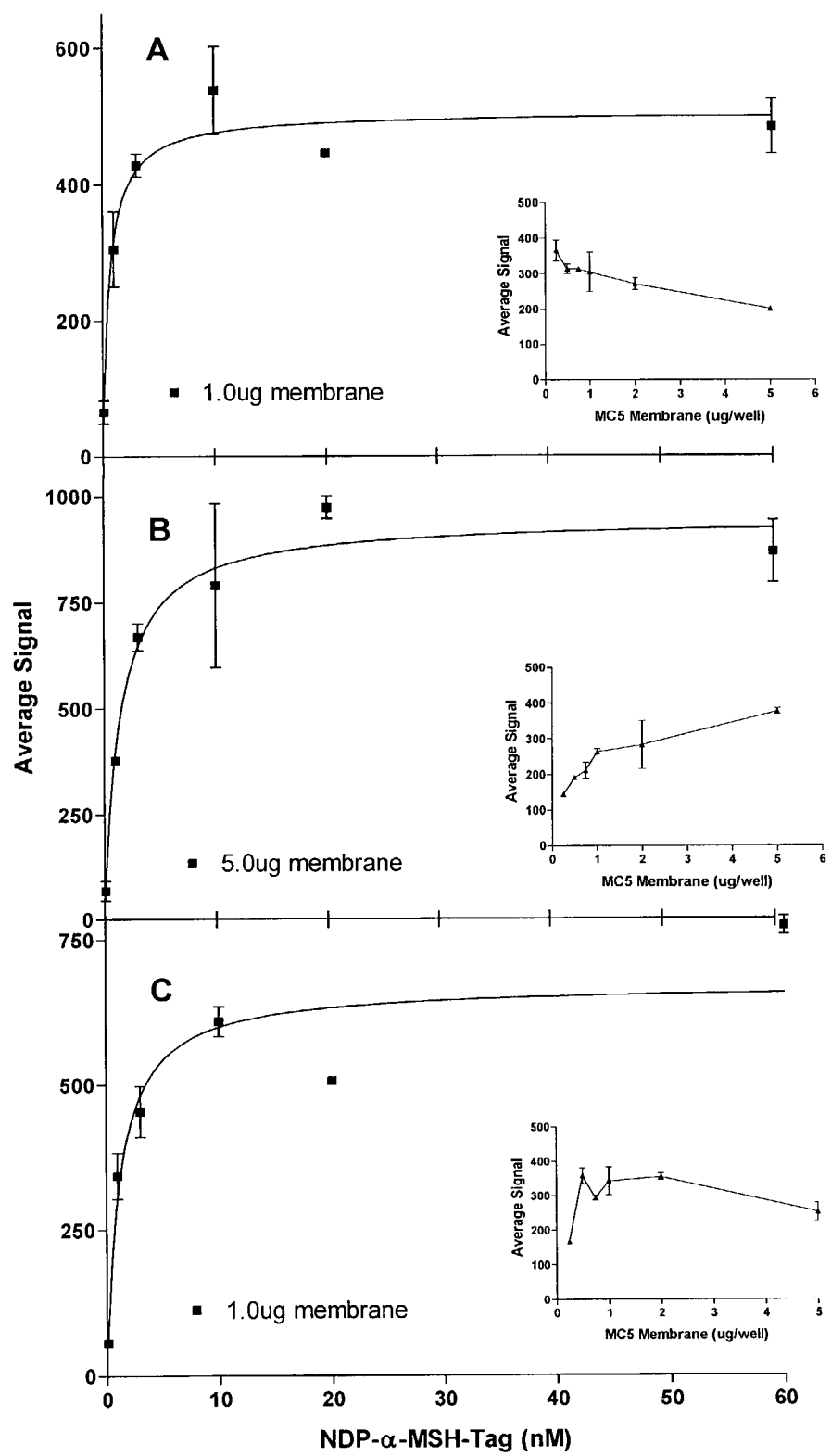

FIG. 7A shows the results of an electrochemiluminescence assay for binding of STAG-NDP-α-MSH to MC5 in passively immobilized membrane fragments. The plot shows average ECL signal (vertical axis) as a function of the concentration of STAG-NDP-α-MSH (nM) (horizontal axis). The insert FIG. 7A shows average ECL signal (vertical axis) as a function of the MC5-containing membrane concentration (µg/well) (horizontal axis) where the concentration of STAG-NDP-α-MSH was fixed at 1 nM.

FIG. 7B shows the results of an electrochemiluminescence assay for binding of STAG-NDP-α-MSH to MC5 where the capture of MC5-containing membranes was mediated by lectins passively adsorbed on the electrode surface. The plot shows average ECL signal (vertical axis) as a function of the concentration of STAG-NDP-α-MSH (nM) (horizontal axis). The insert FIG. 7B shows average ECL signal (vertical axis) as a function of the MC5-containing membrane concentration (µg/well) (horizontal axis) where the concentration of STAG-NDP-α-MSH was fixed at 1 nM.

FIG. 7C shows the results of an electrochemiluminescence assay for binding of STAG-NDP-α-MSH to MC5 where the capture of MC5-containing membranes was mediated by biotinylated lectins preadsorbed on the avidin-coated electrode surface. The plot shows average ECL signal (vertical axis) as a function of the concentration of STAG-NDP-α-MSH (nM) (horizontal axis). The insert FIG. 7C shows average ECL signal (vertical axis) as a function of the MC5-containing membrane concentration (µg/well) (horizontal axis) where the concentration of STAG-NDP-α-MSH was fixed at 1 nM.

Figure 8:
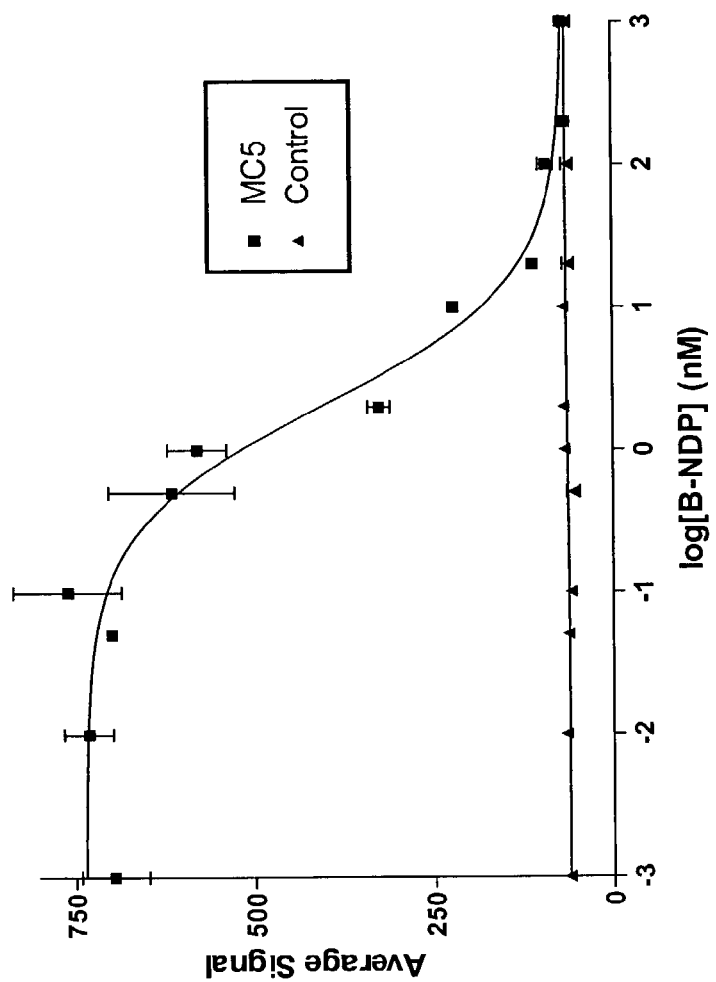

FIG. 8 shows the results of an electrochemiluminescence assay for inhibitors of the binding of STAG-NDP-α-MSH to MC5 in passively immobilized membrane fragments. The plot shows average ECL signal (vertical axis) as a function of the log concentration of unlabelled B-NDP (nM) (horizontal axis).

Figure 9:
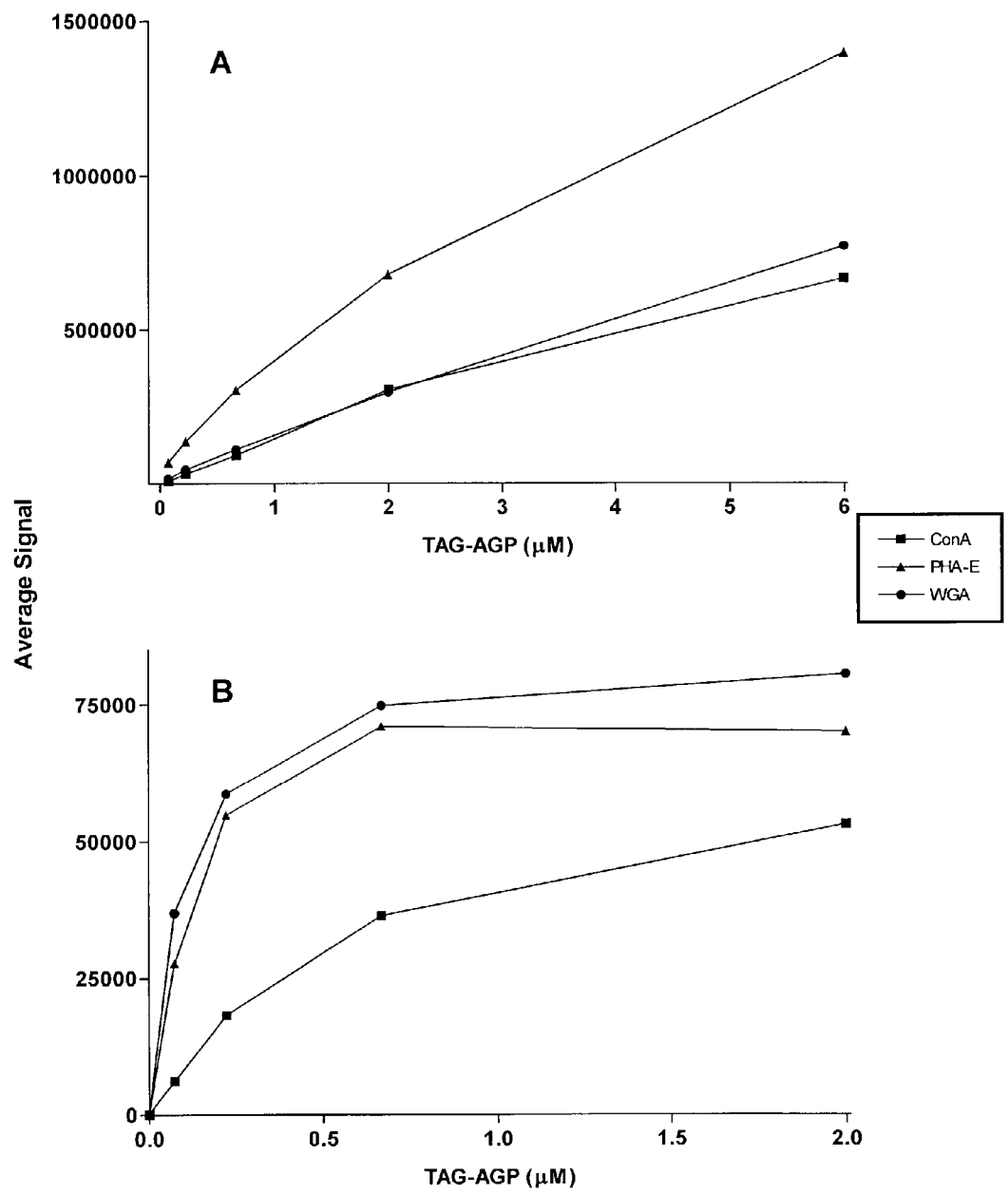

FIG. 9A shows the results of an electrochemiluminescence assay for binding of α-1-Acidglycoprotein (AGP) to passively immobilized lectins. The plot shows average ECL signal (vertical axis) as a function of the concentration of TAG-AGP (nM) (horizontal axis).

FIG. 9B shows the results of an electrochemiluminescence assay for binding of α-1-Acidglycoprotein (AGP) to biotinylated lectins immobilized on avidin-coated surface. The plot shows average ECL signal (vertical axis) as a function of the concentration of TAG-AGP (nM) (horizontal axis).

Figure 10:
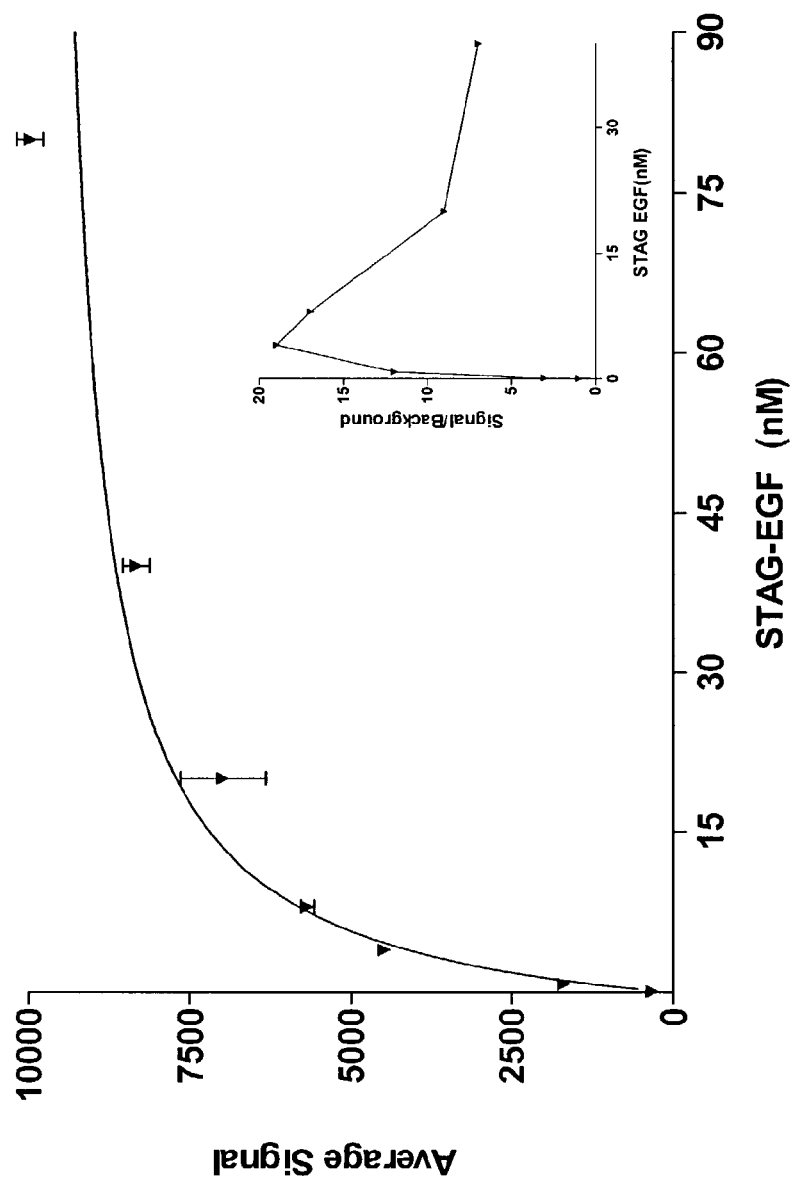

FIG. 10 shows the results of an electrochemiluminescence assay for binding of STAG-EGF to EGFR where the capture of EGFR containing membranes was mediated by biotinylated lectins preadsorbed on the avidin-coated magnetic particles. The plot shows average ECL signal (vertical axis) as a function of the concentration of STAG-EGF (nM) (horizontal axis). The insert of FIG. 10 shows the sensitivity of the assay plotted as ECL signal ration to background (vertical axis) as a function of the concentration of STAG-EGF (nM) (horizontal axis).

5. DETAILED DESCRIPTION OF THE INVENTION

The invention includes a material, preferably a lipid, membrane protein or lipid/protein layer (i.e., a layer that comprises lipid and protein), that is immobilized onto one or more assay electrodes. Preferably, the lipid, membrane protein, or lipid/protein layer is (or is derived from) a biological membrane or synthetic analog thereof. The invention also includes electrodes having membrane proteins immobilized thereon. Such electrodes may be incorporated into a variety of different assay modules suitable for carrying out assays, e.g., assay plates, cassettes, cartridges, devices, etc. Preferably, the electrode is incorporated in the wells of a multi-well assay plate. The assay region or module (e.g., a given well of a multi-well plate) may also comprise additional electrodes. Preferably at least one electrode in an assay region or module (or a well of a multi-well plate) is suitable for use as a working electrode in an electrode induced luminescence assay, at least one electrode is suitable for use as counter electrode in an electrode induced luminescence assay. Optionally, there is at least one electrode that is suitable for use as a reference electrode (e.g., in a three electrode electrochemical system). Preferably, no reference electrode is included.

Lipid or lipid/protein layers immobilized on electrode surfaces may take on a variety of different forms. They may include lipid monolayers, bilayers and/or multilayers. They may include planar membranes, membrane sheets, micelles, membrane vesicles (unilamellar and/or multilamellar), membrane ghosts, liposomes, and/or membrane fragments. They may also include whole cells, organelles, virions, tissue, etc. The exact nature of the lipid or lipid/protein layer is dependent on the nature and composition of the material being immobilized, the immobilization conditions and the nature of the electrode surface. FIG. 1 shows schematic representations of some examples of lipid or lipid/protein layers that can be formed on an electrode.

Figure 1A:
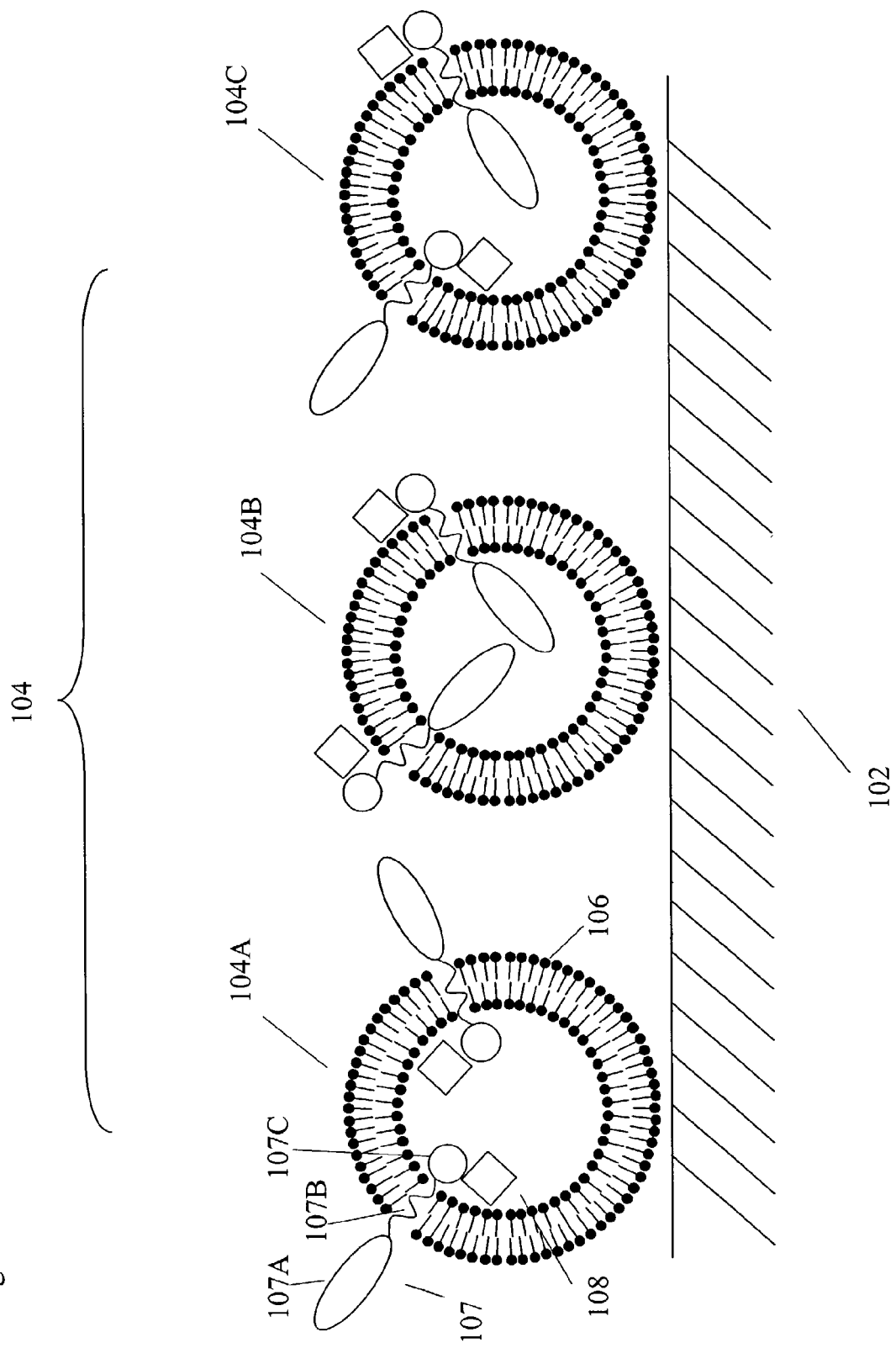
FIG. 1A is a schematic representation of immobilized lipid/protein vesicles according to an embodiment of the invention.

FIG. 1A shows a lipid or lipid/protein layer comprising membrane vesicles (or, in alternate embodiments whole cells, organelles or virions) 104 immobilized on assay electrode 102, e.g., an assay electrode integrated into the well of a multi-well plate. The vesicles comprise lipids 106 in a lipid bilayer and, optionally, integral membrane proteins 107 (having extra-cellular domain 107A, trans-membrane domain 107B and cytoplasmic domain 107C) and/or peripheral membrane proteins 108. Depending on the procedure used to form the vesicles and the lipid/protein layer, the vesicles may present the extra-cellular (or, extra-organelle, etc.) side of the membrane components (e.g., as shown for vesicle 104A), the vesicle may present the cytoplasmic (or, inter-organelle side, etc.) side of the membrane (e.g., as shown for vesicle 104B), and/or the membrane components may be randomly distributed on the inside and outside of the vesicle (e.g., as shown for vesicle 104C (e.g., rejoined sheets in opposite orientations that have closed to form a vesicle)).

Figure 1B:
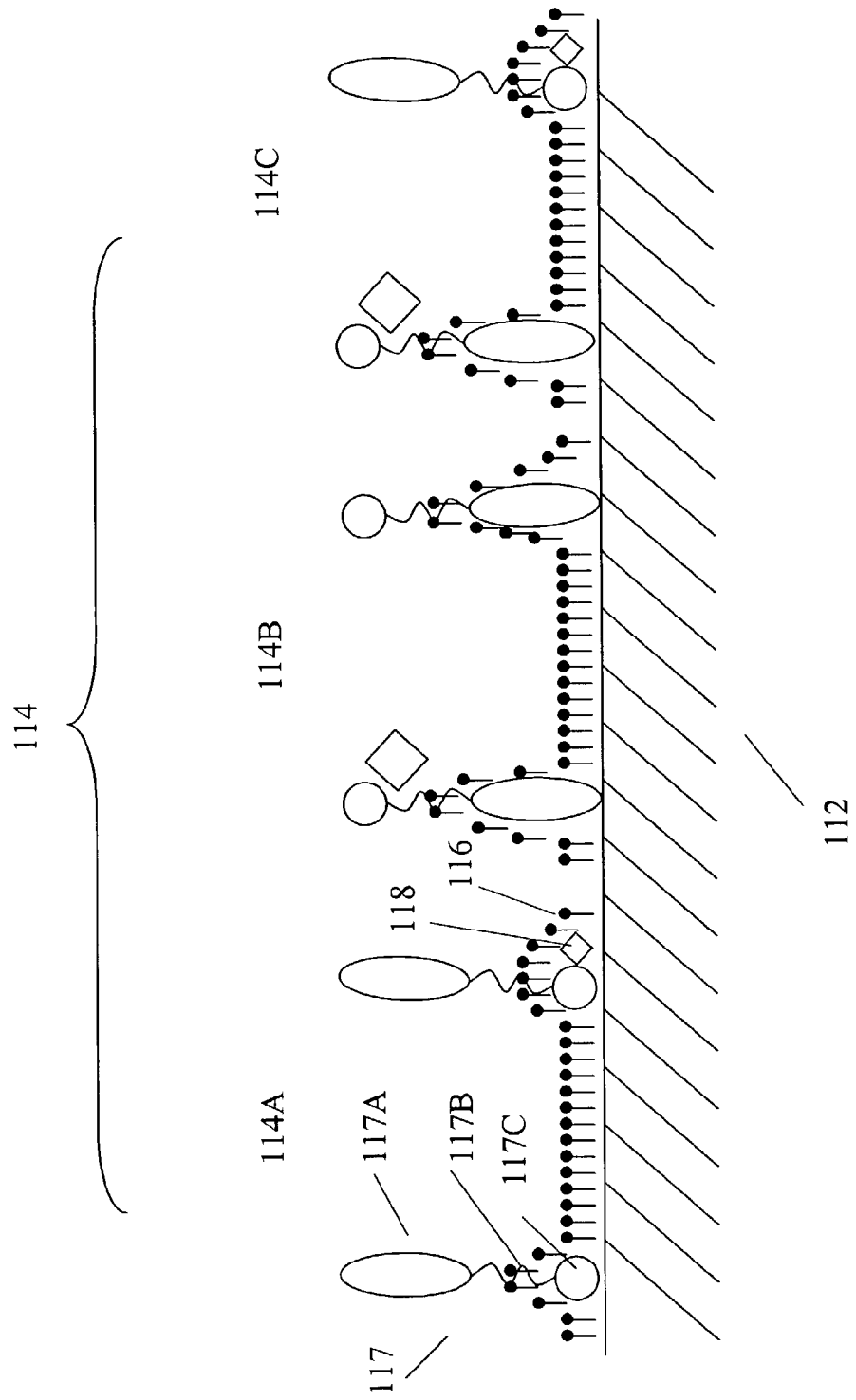
FIG. 1B is a schematic representation of immobilized lipid monolayers according to another embodiment of the invention.

FIG. 1B shows a lipid or lipid/protein layer comprising a lipid monolayer 114 immobilized on assay electrode 112, e.g., an assay electrode integrated into the well of a multi-well plate. The monolayer comprises lipids 116 and, optionally, comprises integral membrane proteins 117 (having extra-cellular domain 117A, trans-membrane domain 117B and cytoplasmic domain 117C) and/or peripheral membrane proteins 118. Depending on the procedure used to form the lipid/protein layer, the monolayer may present the extra-cellular (or, extra-organelle, etc.) side of the membrane components (e.g., as shown for monolayer region 114A), the monolayer may present the cytoplasmic (or, inter-organelle side, etc.) side of the membrane (e.g., as shown for monolayer region 114B), and/or the membrane components may be randomly distributed on the inside and outside of the monolayer (e.g., as shown for monolayer region 114C (e.g., rejoined or adjacent leaflets in opposite orientations)).

Figure 1C:
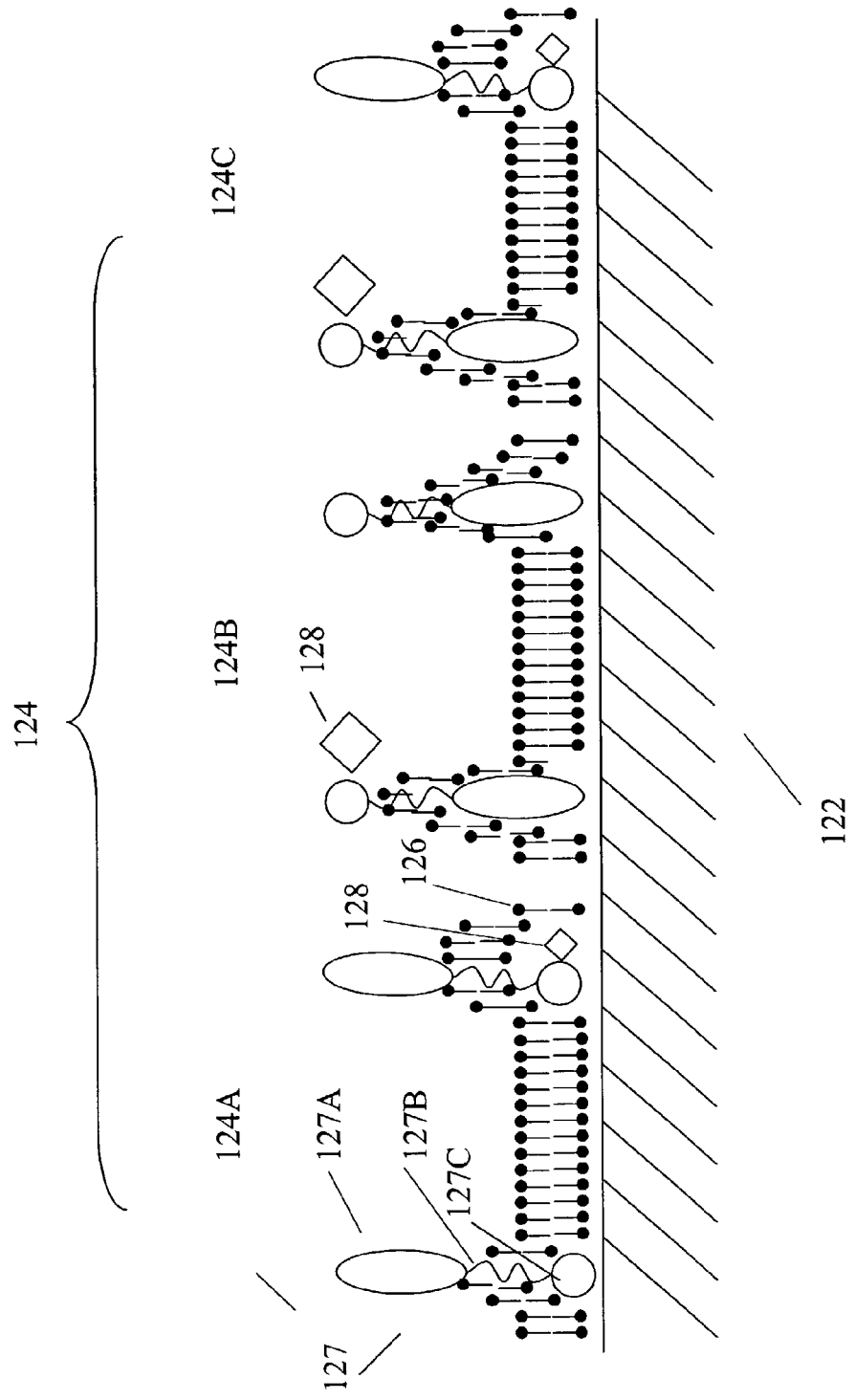
FIG. 1C is a schematic representation of immobilized lipid bilayers according to another embodiment of the invention.

FIG. 1C shows a lipid or lipid/protein layer comprising a lipid bilayer 124 immobilized on assay electrode 122, e.g., an assay electrode integrated into the well of a multi-well plate. The bilayer comprises lipids 126 and, optionally, comprises integral membrane proteins 127 (having extra-cellular domain 127A, trans-membrane domain 127B and cytoplasmic domain 127C) and/or peripheral membrane proteins 128. Depending on the procedure used to form the lipid/protein layer, the bilayer may present the extra-cellular (or, extra-organelle, etc.) side of the membrane components (e.g., as shown for bilayer region 124a), the bilayer may present the cytoplasmic (or, inter-organelle side, etc.) side of the membrane (e.g., as shown for bilayer region 124B), and/or the membrane components may be randomly distributed on the inside and outside of the bilayer (e.g., as shown for bilayer region 124C (e.g., rejoined or adjacent sheets of opposite orientation)).

Figure 1D:
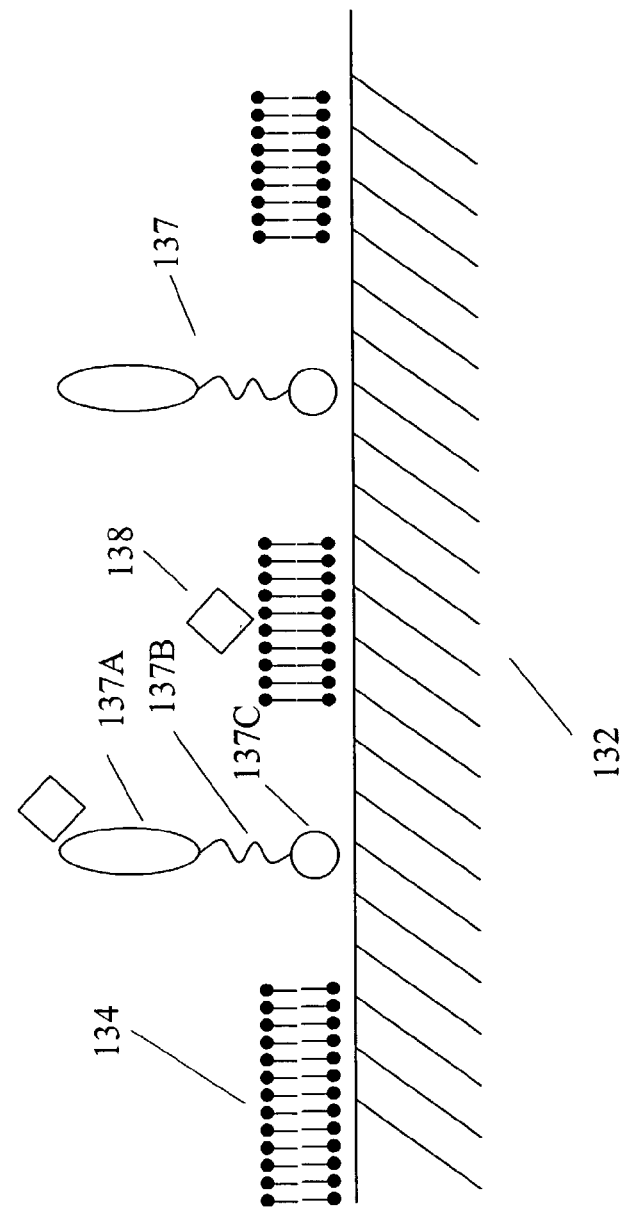
FIG. 1D is a schematic representation of immobilized lipid/protein layers according to another embodiment of the invention.

FIG. 1D shows a lipid/protein layer immobilized on electrode 132, e.g., an assay electrode integrated into the well of a multi-well plate, the lipid/protein layer comprising immobilized lipid regions 134, immobilized integral membrane proteins 137 (having extra-cellular domain 137A, trans-membrane domain 137B and cytoplasmic domain 137C) and, optionally, peripheral membrane proteins 138. Optionally, the lipid regions may be omitted so as to form a protein layer comprising immobilized integral membrane proteins. The integral membrane proteins may be immobilized via association with the lipid regions and/or immobilized by direct interaction (adsorption, specific binding, etc.) with the electrode (as shown).

The immobilized membrane lipid, membrane protein or lipid/protein layers of the invention can be immobilized on electrodes via a variety of interactions including non-specific adsorption (e.g., via non-specific ionic, hydrogen bonding, polar, Van der Waals and/or hydrophobic interactions), covalent bonding, and/or specific binding interactions between binding partners (e.g., ligand/receptor, antibody/antigen, nucleic acid hybridization, biotin/avidin, biotin/streptavidin, lectin/saccharide, metal/ligand, etc.). Microtubules that interact with the membrane lipid, membrane protein or lipid/protein layer can also be used for the immobilization (e.g., by immobilization via interactions with microtubules coated on an electrode). The electrode can also be coated with cell adhesion promoters such as fibronectin, collagen and/or integrins and the membrane lipid, membrane protein or lipid/protein layer immobilized onto the coated surface. Interactions between a lipid/protein layer and an electrode may be mediated through the protein and/or lipid components (e.g., in one embodiment a membrane protein may be held on the electrode via its association with an immobilized lipid layer; in another embodiment it may be directly linked to the electrode). Preferably, the material is immobilized directly onto the electrode, more preferably without the use of an immobilization agent (e.g., a dye, trehalose, etc.). Surprising, a very high percentage of immobilization is achieved using the invention, in particular when the amount of material applied is less than the binding capacity of the surface. Preferably, at least 50 wt %, more preferably at least 65 wt %, even more preferably at least 75 wt %, even more preferably at least 85 wt % and most preferred at least about 90 wt % of the material in the composition applied to the electrode is immobilized.

Figure 1E:
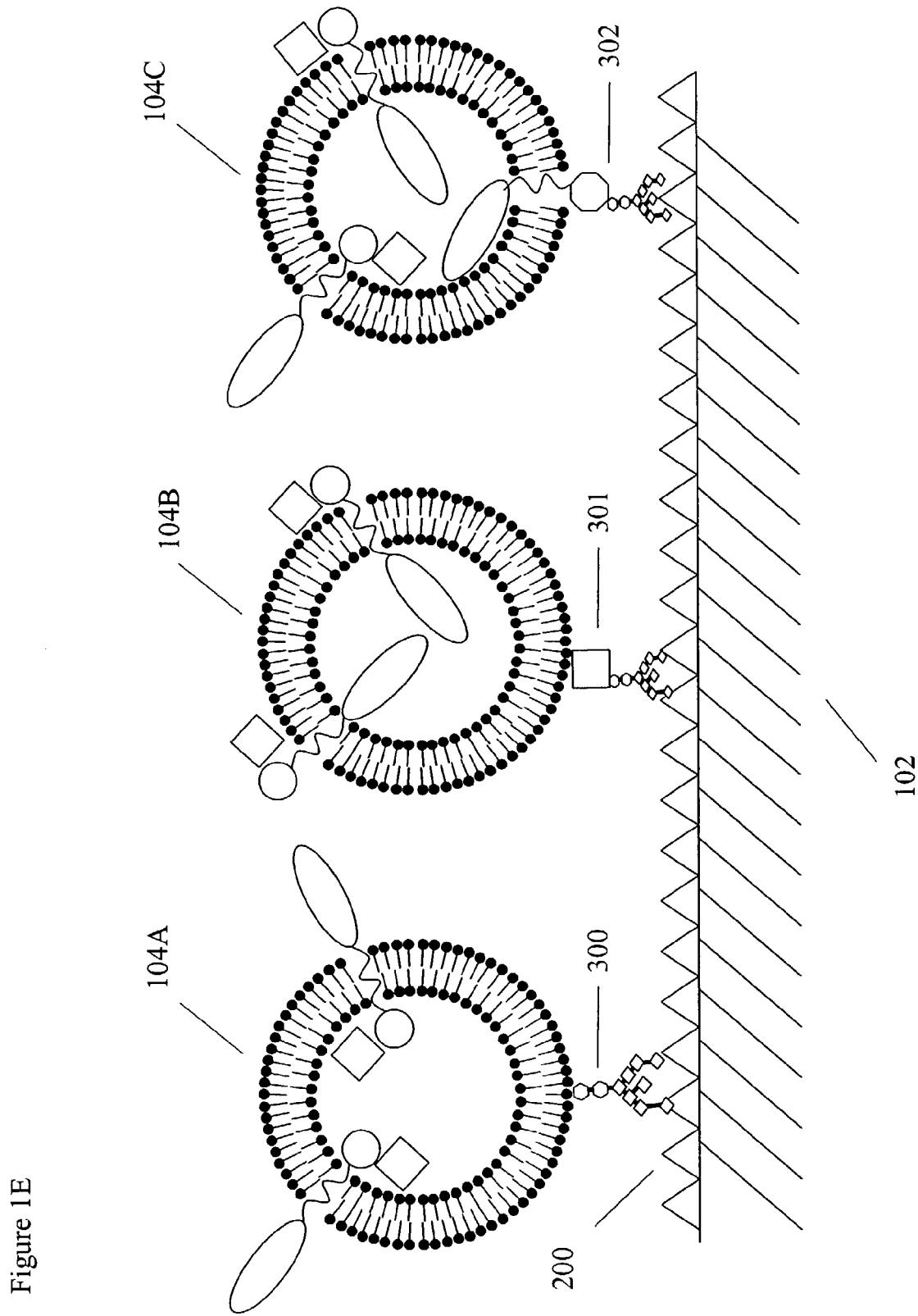
FIG. 1E is a schematic representation of immobilized lipid/protein vesicles according to another embodiment of the invention.

FIG. 1E shows a lipid or lipid/protein vesicles comprising membrane vesicles (or, in alternate embodiments whole cells, organelles or virions) 104 immobilized on assay electrode 102, e.g., an assay electrode integrated into the well of a multi-well plate, where the assay electrode 102 has lectins or antibodies 200 immobilized thereon. Vesicle immobilization proceeds through interactions between polysaccharide chains of glycosylated lipids 300, glycosylated proteins laying on the membrane 301, or glycosylated transmembrane proteins 303 and lectins 200, or alternatively through specific interactions between antigenic polysaccharides, or proteins 301-303 and their respective antibodies 200. The lectin or antibody mediated immobilization can also be used for a lipid or lipid/protein monolayers and bilayers depicted in FIGS. 1B-D.

In one preferred embodiment of the invention, a lipid or lipid/protein layer is directly adsorbed on an electrode surface, preferably on a carbon electrode, more preferably on a carbon composite electrode, most preferably on a carbon ink electrode. In another preferred embodiment of the invention, a lipid or lipid/protein layer is immobilized via the binding of membrane components to antibodies immobilized on the surface of an electrode, preferably on a carbon electrode, more preferably on a carbon composite electrode, most preferably on a carbon ink electrode. In another preferred embodiment, a lipid or lipid/protein layer is immobilized via the binding of sugar groups present in the membrane (e.g., sugars present in membrane associated glycoproteins or glycolipids) to a lectin (e.g., wheat germ agglutinin or ConA) immobilized on an electrode surface, preferably on a carbon electrode, more preferably on a carbon composite electrode, most preferably on a carbon ink electrode. More specifically, the invention relates to processes that improve the binding properties of the surface by coating the surface with lectins, preferably plant lectins, such as *Aegopodium podagraria* lectin (APA), *Aleuria Aurantia* Lectin (AAL), *Allium Sativum* Lectins (ASA I and ASA II), *Allium Ursinum* Lectins (AUA I and II), *Amaranthus Caudatus* Lectin (ACL, ACA), *Arum Maculatum* Lectin (AMA), *Bauhinia Purpurea* Lectin (BPL), *Bryonia dioica* Lectin (BDA), Calsepa, Concanavalin A (ConA), *Chelidonium Majus* Lectin (CMA), *Cladrastis Lutea* Lectins (CLA I and II), *Colchicum Autumnale* Lectin (CAA), *Datura*

Stramonium Lectin (DSL), *Dolichos Biflorus* Agglutinin (DBA), *Erythrina Cristagalli* Lectin (ECL, ECA), *Euonymus Europacus* Lectin (EEL), Favin, *Galanthus Nivalis* Lectins (GNA and GNL), *Griffonia (Bandeiraea) Simplicifolia* Lectins I and II, GSL I—isolectin B4, Hippeastrum Hybrid Lectin (HHL, AL), Iris Hybrid Lectin (IRA), Jacalin, Lens Culinaris Agglutinin (LCA, LcH), *Listera ovata* Lectin (LOA), *Lotus Tetragonolobus* Lectin (LTL), *Lycopersicon Esculentum* (Tomato) Lectin (LEL, TL), *Maackia Amurensis* Lectins I and II (MAL I and MAL II), *Maclura Pomifera* Lectin (MPL), *Narcissus Pseudonarcissus* Lectin (NPL, NPA), Peanut Agglutinin (PNA), *Phaseolus Vulgaris* Agglutinin (PHA), *Phytolacca Americana* Mitogen (PWM), *Pisum Sativum* Agglutinin (PSA), *Polygonatum Multiflorum* Lectin (PMA), *Psophocarpus Tetragonolobus* Lectins I and II, Ricin A and B Chains, Ricinus Communis Agglutinins I and II, Sambucus Nigra Lectin (SNA, EBL), Solanum Tuberosum (Potato) Lectin (STL, PL), *Sophora Japonica* Agglutinin (SJA), Soybean Agglutinin (SBA), *Urtica dioica* Lectin (UDA), *Ulex Europaeus* Agglutinins I and II (UEA I and II), *Vicia Villosa* Lectin (VVL, VVA), Wheat Germ Agglutinin (WGA) and *Wisteria Floribunda* Lectin (WFA, WFL). More preferably plant lectins are chosen that are readily available and recognize specific polysaccharide structures, such lectins include AAL, ASA I and II, AUA I and II, Con A, CAA, EEL, Jacalin, LCA, LcH, LEL, PHA, PWM, PSA, Ricin Communis Agglutinins I and II, SNA, STL, PL and WGA, more preferably, pokeweed mitogen (PWM) or phytohemagglutinin (PHA) (the plant proteins extracted from *Phytolacca Americana* and *Phaseolus Vulgaris* respectively), most preferably the PHA-E isoform of PHA.

Pokeweed mitogen was found to be an excellent capture reagent for capturing membrane fragments because it efficiently captures membrane fragments from a variety of different cell types and it retains a high degree of capture activity on immobilization while preserving a high degree of activity in the immobilized membrane. Accordingly, the invention includes solid phase supports having pokeweed mitogen immobilized thereon. The invention also includes pokeweed mitogen coated solid phase supports having biomaterials (e.g., lipid or lipid/protein layers) immobilized thereon, the biomaterials being immobilized via binding interactions to the pokeweed mitogen. Solid phase supports may include particulate matter (such as magnetic particles), electrode materials (as described in more detail below), plastics (e.g., polypropylene, polystyrene, polyethylene, nylon, etc.), glass, ceramics, etc. One preferred embodiment is a multi-well plate comprising at least one well that has pokeweed mitogen immobilized on a surface thereof. The invention also includes methods for immobilizing biomaterials on pokeweed mitogen coated solid phases comprising the step of contacting the solid phase with the biomaterial. The invention also includes methods for conducting assays that include the steps of immobilizing a biomaterial on a pokeweed mitogen coated solid phase and measuring the amount or activity (e.g., binding activity or enzymatic activity) of said biomaterial. In a preferred embodiment of the invention, the biomaterial is used as a binding reagent for measuring, via a binding assay, an analyte in a sample.

The performance of pokeweed mitogen from commercial sources was found to vary from lot to lot and it was important to screen lots for preparations that performed adequately. The performance appeared to correlate with the ratio of protein to carbohydrate in the purified lectin preparation (which could vary from 0.1 to 9 by weight). Applicants hypothesize that the lectins that were overloaded with carbohydrates did not have accessible binding sites. Accordingly, it is preferred that the pokeweed mitogen preparation used in the methods and/or devices of the invention be purified from endogenous carbohydrates to give a protein/carbohydrate ratio greater than or equal to 1.0, more preferably greater than or equal to 2.5 and most preferably greater than or equal to 9.0.

In another preferred embodiment, a lipid or lipid/protein layer is immobilized via the binding of a labeled component of the membrane (e.g., a biotin or hapten labeled lipid, protein or sugar) to a binding reagent (e.g., streptavidin, avidin or an antibody) immobilized on an electrode surface, preferably on a carbon electrode, more preferably on a carbon composite electrode, most preferably on a carbon ink electrode. The membrane could be labeled by the physical insertion of the hydrophobic label into the membrane bilayer or by chemical modification of the membrane by standard chemical modification techniques such as reaction with an NHS ester.

In another preferred embodiment, a lipid or lipid/protein layer is immobilized via the binding of a component of the membrane to a microtubule or cell adhesion promoter immobilized on an electrode surface, preferably on a carbon electrode, more preferably on a carbon composite electrode, most preferably on a carbon ink electrode.

The electrode of the invention may include a spacer layer between the electrode and an immobilized lipid or lipid/protein layer. Such a layer may function, e.g., as a chemical linker for holding the layer to the electrode and/or as a hydrophilic spacer volume (i.e., a spacer volume that reduces direct contact between the electrode surface and the lipid/protein layer, allows both sides of the lipid/protein layer to contact a water or water-like environment (e.g., when the spacer layer comprises a hydrogel) and/or allows the components of a lipid/protein layer to retain the mobility observed in, e.g., biological membranes. See, PCT Patent Publication WO99/51984 and U.S. Pat. Nos. 5,637,201; 5,401,378; and 5,766,960, hereby incorporated by reference.

In some embodiments of the invention, the immobilized lipid, protein or lipid/protein layers are fixed and/or cross-linked so as to provide greater stability. Cross-links may include i) cross-links between membrane components (e.g., lipids, proteins and/or sugars) and chemical moieties on the electrode surface and ii) cross links between membrane components themselves. Cross-linking and/or fixing may be accomplished by a variety of techniques, e.g., techniques known in the arts of tissue fixing, sample preparation for microscopy, bioconjugate chemistry, affinity-labeling and the preparation of cross-linked lipid membranes. Fixing may be accomplished by treating the immobilized layers with dehydrating agents such as alcohols. Useful cross-linking reagents include cross-linking reagents that comprise one or more functional groups capable of reacting with components of a lipid/protein layer or an electrode surface (e.g., imidoesters, active esters such as NHS esters, maleimides, α-halocarbonyls, disulfides such as pyridyldithiols, carbodiimides, arylazides, amines, thiols, carboxylates, hydrazides, aldehydes or ketones, active carbamates, glyoxals, etc.). In some applications it may be advantageous to use photo-reactive cross-linkers (such as arylazides) so as to better control the cross-linking process. Exemplary cross-linking agents include homo- and hetero-bifunctional cross-linking agents such as those sold by Pierce Chemical Co. and/or described in the 1994 Pierce Catalog and Handbook (Pierce Chemical Co., Rockford, Ill., 1994), the chapters relating to cross-linking agents hereby incorporated by reference. Lipid monolayers and bilayers may be cross-linked by chemically cross-linking lipid head-groups and/or tail groups (e.g., by including lipids with tails comprising photochemically cross-linkable groups such as alkene or alkyne groups and/or by including lipids that can span bilayer lipid membranes). See, U.S. Pat. No. 5,637,201, hereby incorporated by reference.

During the fixing and/or cross-linking of immobilized lipid/protein layers, and in particular, biological structures comprising biological membranes, it may be advantageous to treat the layer with a permeabilizing layer so that internal components of the structure are exposed to solution. Such treatment allows for the measurement of such internal components and/or for their use as binding reagents to capture materials in solution. The permeabilization of fixed biological structures may be accomplished using standard permealization methods and reagents used in histochemistry; we have found that fixing tissues on electrodes with alcohol not only forms a stable tissue layer on the electrode but also permeabilizes the cells and allows for the conduct of assays of internal cellular components such as phosphotyrosine containing proteins.

The immobilized lipid, protein and/or lipid/protein layers of the invention may include a variety of lipids and/or proteins. Preferably, the components (e.g., receptors, proteins, etc.) have a biological activity of interest and retain at least some (preferably at least 20%, more preferably at least 25%, more preferably at least 30%, even more preferably at least 35%, even more preferably at least 40% and most preferred at least 50%) after immobilization.

In one specific embodiment of the present invention whole cells are immobilized on the surface. The activity of the enzymes of interest within the immobilized cells is retained upon immobilization at the level of at least of 20%, more preferably at least 25%, more preferably at least 30%, even more preferably at least 35%, even more preferably at least 40% and most preferred at least 50%. The cells may comprise established cell lines, or be derived from specific normal tissues, or tissues of known, or unidentified pathology.

Preferred lipid components include phospholipids (e.g., phosphatidyl choline, phosphatidyl serine, phosphatidyl ethanolamine, phosphatidyl inositides including phosphatidyl inositol phosphates, phosphatidyl glycerols and phosphatidic acid), lysophospholipids, ceramides, sphingomyelins, sphingolipids, glycosphingolipids, glycoceramides, sterols (e.g., cholesterol), fatty acids and bile salts. Lipids having long chain hydrocarbon tails may comprise saturated, monounsaturated or poly unsaturated tails including myristyl, palmityl, stearyl, arachidyl, behenyl, lignoceryl, cerotyl, palmitoleoyl, oleoyl, vaccenyl, linoleoyl, and arachidonyl chains. Preferred protein components include single transmembrane receptors with intrinsic tyrosine kinase activity; non-tyrosine kinase transmembrane receptors (e.g., transferrin receptor); G-protein coupled receptors (GPCR); GPCR effector proteins (e.g., adenylate cyclase); organelle-bound GTPases; guanine nucleotide exchange factors (GEFs); GTPase activating proteins (GAPs); cytokine/chemokine receptors; cell adhesion molecules (e.g., VCAM, integrins); cytoplasmic peripheral membrane protein kinases (e.g., src); intracellular protein kinase adaptor/docking proteins (e.g., insulin receptor substrate 1, GRB2); ion channels (e.g. nicotinic acetylcholine receptor and cystic fibrosis transmembrane conductance regulator (CFTR)); passive transporter proteins (e.g., glucose transporters); active (ATP-driven) transporters; ion-linked transporters (e.g., Na+/glucose channels); glycosyltranferases; and glycoprotein modifying enzymes.

According to one preferred embodiment, the immobilized material comprises protein. Preferably, the resultant electrode comprises between 0.1 micrograms to 10 micrograms of total protein per 0.322 in$^2$ electrode, more preferably between 0.1 micrograms to 5 micrograms, more preferably between 0.1 micrograms to 1 micrograms, even more preferably 0.3 micrograms to 0.7 micrograms and most preferred about 0.5 micrograms (i.e., preferably between 0.3 micrograms to 30 micrograms of total protein per 1 in$^2$ electrode, more preferably between 0.3 micrograms to 15 micrograms, more preferably between 0.3 micrograms to 3 micrograms, even more preferably 1 micrograms to 2 micrograms and most preferred about 1.5 micrograms).

The invention includes the immobilization of a variety of materials onto the one or more electrodes. The materials that can be immobilized include biological structures that comprise biological membranes (e.g., multi-cell organisms, biological tissue, cells, organelles, viral particles, vesicles released by cells such as synaptic vesicles and virus-induced membrane-enclosed viral particles, etc.) and biological membranes derived therefrom. Such biological structures may be (or be derived from) animals, plants, yeast, fungi, viruses, etc. and may be derived from a variety of different tissue types including hair, fur, feathers, skin, dermis, endodermis, nerve tissue, blood cells, internal organs, lymphatic tissue, cardiovascular tissue, respiratory tissue, kidney and urinary tract tissue, gastro-intestinal tissue, hepatic tissue, musculo-skeletal tissue, tissue from the endocrine system, connective tissue, tumors, and fractions thereof. Cells may be eukaryotic or prokaryotic. Cells may be live or dead. Cells that can be immobilized include cells derived from an organism (e.g., from a tissue sample or biopsy) and cells grown in culture (including immortalized cell lines and hybridomas). Viable cells immobilized on the surface of an electrode may be allowed to grow while in contact with the surface. Examples of organelles that may be immobilized include nuclei, endosomes, clathrin-coated vesicles, endoplasmic reticulum fragments, synaptic vesicles, golgi fragments, mitochondria, peroxisomes, lysosomes, etc. Materials that may be immobilized include biological membranes, e.g., biological membranes derived from organisms, tissue, cells, organelles or virus particles, including membranes, membrane fragments, membrane sheets, membrane vesicles, membrane ghosts, membrane subdomains (e.g., membrane rafts), etc. Organelles and other cell-derived materials may be immobilized from crude samples, e.g., crude cell lysates or cell supernatants. Alternatively, these materials may first be purified, e.g., by centrifugation, gradient centrifugation, chromatography, etc. Materials that may be immobilized also include synthetic analogs of biological membranes, e.g., micelles or membranes made by reconstituting biologically derived and/or synthetic lipids into lipid monolayers, bilayers and/or liposomes. Such synthetic biological membranes may also include reconstituted membrane proteins and/or receptors. Methods for making reconstituted lipid membranes, optionally comprising membrane proteins, are known in the art and include mixing detergent solubilized lipids and membrane proteins and removing the detergent (e.g., by dialysis) so as to form lipid membranes comprising the membrane proteins.

In a preferred embodiment of the invention, lipid or lipid/protein layers on electrodes are formed by immobilizing on the electrode a material comprising a biological structure comprising a biological membrane, a biological membrane, and/or a synthetic biological membrane (e.g., the biological structures, biological membranes, and/or synthetic biological membranes as described above). In selected embodiments, this immobilization involves the formation of covalent linkages or cross-links between the material and functional groups on the electrode surface, the selective binding of components of the material to binding reagents immobilized on the electrode and/or, most preferably, the passive adsorption of the material to the electrode surface. In an alternate embodiment, membrane lipids and/or proteins are immobilized via the formation of covalent bonds, via specific binding interactions and/or via the non-specific adsorption of detergent solubilized membrane lipids and/or proteins. Such immobilization may occur in the presence of the detergent. Alternately, the immobilization comprises the step of removing the detergent (e.g., by dialysis or via a detergent selective affinity matrix) so as to promote the formation of membranes and/or the adsorption of hydrophobic components. In another alternate embodiment, one or more protein, lipid and/or lipid/protein films are transferred to the electrode (e.g., by transferring films formed at the air-water interface by Langmuir-Blodgett techniques, most preferably by sequentially transferring two lipid monolayers so as to form a lipid bilayer film, the films optionally comprising membrane proteins).

Preferably, the electrodes of the invention have a high binding capacity for membranes and/or membrane components. For example, for immobilized layers comprising cell-derived components, there may be a plurality of cell equivalents of the component per electrode/assay domain/well (e.g., preferably greater than approximately 10 cell equivalents, more preferably approximately 100 cell equivalents, even more preferably approximately 1000 cell equivalents, even more preferably approximately 10,000 cell equivalents or higher) in the assay. Preferably, the component is derived from a cell selected for presenting a large number of said components. For example, receptors (e.g., receptors in cell membrane fragments) are preferably derived from cells having at least $10^3$ receptors per cell membrane, more preferably at least $10^4$ receptors per cell membrane, more preferably at least 1 receptors per cell membrane, even more preferably at least $10^6$ receptors per cell membrane.

Surprisingly, the use of electrode induced luminescence, particularly electrochemiluminescence, allows for very low detection limits. Thus, membranes having low concentrations of active receptors may also be used in the present invention. Preferably, the assay region (e.g., well of a multi-well plate) comprises less than 100,000 cells per well, more preferably less than 50,000 cells per well, even more preferably less than 10,000 cells per well and most preferred less than about 1,000 cells per well. According to another embodiment, the assay region (e.g., well of a multi-well plate) comprises less than $10^{12}$ receptors, more preferably less than $10^{10}$ receptors, even more preferably less than $10^8$ receptors, and most preferably less than $10^6$ receptors per well.

According to one embodiment, the assay electrode is incorporated in an assay module, e.g., an electrode located in one or more wells of a multi-well plate. Suitable assay modules, including multi-well assay modules, and method of using and systems incorporating the same are set forth in U.S. Provisional Application Ser. No. 60/301,932 entitled "Assay Plates, Reader Systems and Methods for Luminescence Test Measurements", filed Jun. 29, 2001 (see Sections 3, 4 and 5.1-5.6), hereby incorporated by reference. According to one preferred embodiment of the invention, an assay module or plate comprises one or more (preferably two or more, 6 or more, 24 or more, 96 or more, 384 or more, 1536 or more or 9600 or more) assay wells, assay chambers and/or assay domains (e.g., discrete locations on a module surface where an assay reaction occurs and/or where an assay signal is emitted; typically an electrode surface, preferably a working electrode surface). According to a particularly preferred embodiment, the assay plate is a multi-well assay plate having a standard well configuration (e.g., 6 well, 24 well, 96 well, 384 well, 1536 well, 6144 well or 9600 well).

The invention also includes arrays of lipid and/or lipid/protein layers on electrodes and modules comprising such arrays. In one embodiment of the invention, an array comprising a plurality of assay domains is formed on an electrode surface, the assay domains comprising the lipid and/or lipid/protein layers of the invention. Preferably, the array is formed by patterned deposition of solutions of biomaterials, however, other standard techniques for biological array formation may be used. In electrode induced luminescence assays, luminescence generated from an array on a single electrode is preferably measured using a camera (e.g., a CCD or cmos camera) or other imaging detector. In an alternative embodiment of the invention, an array of lipid and/or lipid/protein layers is formed on a patterned array of independently addressable electrodes. In this case, luminescence can be measured with a single non-imaging detector such as a photomultiplier tube, phototransistor or photodiode by inducing luminescence at the different electrodes at different times. In an especially preferred embodiment, the arrays of lipid and/or lipid/protein layers are patterned on electrodes in the wells of multi-well plates.

In one preferred embodiment, patterned arrays are formed by patterned immobilization of a variety of tissue types and/or cell types (or membrane fragments, organelles and/or other cellular components derived therefrom) one the surface(s) of one or more electrodes, preferably one or more electrodes comprising elemental carbon, more preferably one or more carbon composite electrodes, most preferably one or more carbon ink electrodes. Such arrays and modules including such arrays allow for a variety of analyses such as differential tissue/cell typing, differential measurements of protein expression, simultaneous screening of potential drug candidates or toxins against a plurality of cell targets, etc.

One aspect of the invention relates to the immobilization of materials, preferably lipid/protein layers, on electrodes having improved electrode compositions and surfaces and assay modules comprising these electrode compositions and surfaces. Electrodes in the present invention are preferably comprised of a conductive material. The electrode may comprise a metal such as gold, silver, platinum, nickel, steel, iridium, copper, aluminum, a conductive alloy, or the like. They may also comprise oxide coated metals (e.g. aluminum oxide coated aluminum). Electrodes may comprise non-metallic conductors such as conductive forms of molecular carbon. Electrodes may also be comprised of semiconducting materials (e.g. silicon, germanium) or semi-conducting films such as indium tin oxide (ITO), antimony tin oxide (ATO) and the like. Electrodes may also be comprised of mixtures of materials containing conducting composites, inks, pastes, polymer blends, metal/non-metal composites and the like. Such mixtures may include conductive or semi-conductive materials mixed with non-conductive materials. Preferably, electrode materials are substantially free of silicone-based materials.

Electrodes (in particular working electrodes) used in assay modules of the invention are advantageously able to induce luminescence from luminescent species. Preferable materials for working electrodes are materials able to induce electrochemiluminescence from Ruthenium-tris-bipyridine in the presence of tertiary alkyl amines (such as tripropyl amine). Examples of such preferred materials include platinum, gold, ITO, carbon, carbon-polymer composites, and conductive polymers.

Preferably, the electrodes are carbon electrodes, i.e., electrodes comprising elemental carbon-based materials such as carbon, carbon black, graphitic carbon, carbon nanotubes, carbon fibrils, graphite, carbon fibers and mixtures thereof. Advantageously, they may be comprised of conducting carbon-polymer composites, conducting particles dispersed in a matrix (e.g. carbon inks, carbon pastes, metal inks), and/or conducting polymers. One preferred embodiment of the invention is an assay module, preferably a multi-well plate, having electrodes (e.g., working and/or counter electrodes) that comprise carbon, preferably carbon layers, more preferably screen-printed layers of carbon inks. Some useful carbon inks include materials produced by Acheson Colloids Co. (e.g., Acheson 440B, 423ss, PF407A, PF407C, PM-003A, 30D071, 435A, Electrodag 505SS, and Aquadag™), E.I. Du Pont de Nemours and Co. (e.g., Dupont 7105, 7101, 7102, 7103, 7144, 7082, 7861D, and CB050), Conductive Compounds Inc (e.g., C-100), and Ercon Inc. (e.g., G-451).

In another preferred embodiment, the electrodes of the invention comprise carbon fibrils. The terms "carbon fibrils", "carbon nanotubes", single wall nanotubes (SWNT), multi-wall nanotubes (MWNT), "graphitic nanotubes", "graphitic fibrils", "carbon tubules", "fibrils" and "buckeytubes", all of which terms may be used to describe a broad class of carbon materials (see Dresselhaus, M. S.; Dresselhaus, G.; Eklund, P. C.; "Science of Fullerenes and Carbon Nanotubes", Academic Press, San Diego, Calif., 1996, and references cited therein). The terms "fibrils" and "carbon fibrils" are used throughout this application to include this broad class of carbon-based materials. Individual carbon fibrils as disclosed in U.S. Pat. Nos. 4,663,230; 5,165,909; and 5,171,560 are particularly advantageous. They may have diameters that range from about 3.5 nm to 70 nm, and length greater than $10^2$ times the diameter, an outer region of multiple, essentially continuous, layers of ordered carbon atoms and a distinct inner core region. Simply for illustrative purposes, a typical diameter for a carbon fibril may be approximately between about 7 and 25 nm, and a typical range of lengths may be 1000 nm to 10,000 nm. Carbon fibrils may also have a single layer of carbon atoms and diameters in the range of 1 nm-2 nm. Electrodes of the invention may comprise one or more carbon fibrils, e.g., in the form of a fibril mat, a fibrinl aggregate, a fibril ink, a fibrinl composite (e.g., a conductive composite comprising fibrils dispersed in an oil, paste, ceramic, polymer, etc.). One preferred embodiment of the invention relates to a multi-well plate comprising a substrate comprising a carbon nanotube-containing composite (preferably, carbon nanotubes dispersed in a polymeric matrix), wherein the surface of the substrate is etched to expose the carbon nanotubes, thereby forming one or more working electrodes.

Electrodes may be formed into patterns by a molding process (i.e., during fabrication of the electrodes), by patterned deposition, by patterned printing, by selective etching, through a cutting process such as die cutting or laser drilling, and/or by techniques known in the art of electronics microfabrication. Electrodes may be self supporting or may be supported on another material, e.g. on films, plastic sheets, adhesive films, paper, backings, meshes, felts, fibrous materials, gels, solids (e.g. metals, ceramics, glasses), elastomers, liquids, tapes, adhesives, other electrodes, dielectric materials and the like. The support may be rigid or flexible, flat or deformed, transparent, translucent, opaque or reflective. Preferably, the support comprises a flat sheet of plastic such as acetate or polystyrene. Electrode materials may be applied to a support by a variety of coating and deposition processes known in the art such as painting, spray-coating, screen-printing, ink-jet printing, laser printing, spin-coating, evaporative coating, chemical vapor deposition, etc. Supported electrodes may be patterned using photolithographic techniques (e.g., established techniques in the microfabrication of electronics), by selective etching, and/or by selective deposition (e.g., by evaporative or CVD processes carried out through a mask). In a preferred embodiment, electrodes are comprised of extruded films of conducting carbon/polymer composites. In another preferred embodiment, electrodes are comprised of a screen printed conducting ink deposited on a substrate. Electrodes may be supported by another conducting material. Advantageously, screen printed carbon ink electrodes are printed over a conducting metal ink (e.g., silver ink) layer so as to improve the conductivity of the electrodes.

According to one preferred embodiment of the invention, the electrode surface (preferably a working electrode surface of an assay module or assay plate) is bounded by a dielectric surface, the dielectric surface being raised or lowered (preferably, raised) and/or of different hydrophobicity (preferably, more hydrophobic) than the electrode surface. Preferably, the dielectric boundary is higher, relative to the electrode surface, by 0.5-100 micrometers, or more preferably by 2-30 micrometers, or most preferably by 8-12 micrometers. Even more preferably, the dielectric boundary has a sharply defined edge (i.e., providing a steep boundary wall and/or a sharp angle at the interface between the electrode and the dielectric boundary).

Preferably, the first electrode surface has a contact angle for water 10 degrees less than the dielectric surface, preferably 15 degrees less, more preferably 20 degrees less, more preferably 30 degrees less, even more preferably 40 degrees less, and most preferred 50 degrees less. One advantage of having a dielectric surface that is raised and/or more hydrophobic than the electrode surface is in the reagent deposition process where the dielectric boundary may be used to confine a reagent within the boundary of the electrode surface. In particular, having a sharply defined edge with a steep boundary wall and/or a sharp angle at the interface between the electrode and dielectric boundary is especially useful for "pinning" drops of solution and confining them to the electrode surface. In an especially preferred embodiment of the invention, the dielectric boundary is formed by printing a patterned dielectric ink on and/or around the electrode, the pattern designed so as to expose one or more assay domains on the electrode. Most preferably, an array of holes in a dielectric layer is used to form an array of assay domains and to confine reagents in the assay domains during the patterned deposition of an array of lipid and/or lipid/protein layers.

Electrodes may be modified by chemical or mechanical treatment to improve the immobilization of reagents and/or membranes. The surface may be treated to introduce functional groups for immobilization of reagents and/or membranes or to enhance its adsorptive properties. Surface treatment may also be used to influence properties of the electrode surface, e.g., the spreading of water on the surface or the kinetics of electrochemical processes at the surface of the electrode. Techniques that may be used include exposure to electromagnetic radiation, ionizing radiation, plasmas or chemical reagents such as oxidizing agents, electrophiles, nucleophiles, reducing agents, strong acids, strong bases and/or combinations thereof. Treatments that etch one or more components of the electrodes may be particularly beneficial by increasing the roughness and therefore the surface area of the electrodes. In the case of composite electrodes having conductive particles or fibers (e.g., carbon particles or fibrils) in a polymeric matrix or binder, selective etching of the polymer may be used to expose the conductive particles or fibers.

One particularly useful embodiment is the modification of the electrode, and more broadly a material incorporated into the present invention by treatment with a plasma, specifically a low temperature plasma, also termed glow-discharge. The treatment is carried out in order to alter the surface characteristics of the electrode, which come in contact with the plasma during treatment. Plasma treatment may change, for example, the physical properties, chemical composition, or surface-chemical properties of the electrode. These changes may, for example, aid in the immobilization of reagents and/or membranes, reduce contaminants, improve adhesion to other materials, alter the wettability of the surface, facilitate deposition of materials, create patterns, and/or improve uniformity. Examples of useful plasmas include oxygen, nitrogen, argon, ammonia, hydrogen, fluorocarbons, water and combinations thereof. Oxygen plasmas are especially preferred for exposing carbon particles in carbon-polymer composite materials. Oxygen plasmas may also be used to introduce carboxylic acids or other oxidized carbon functionality into carbon or organic materials (these may be activated, e.g., as active esters or acyl chlorides) so as to allow for the coupling of reagents. Similarly, ammonia-containing plasmas may be used to introduce amino groups for use in coupling to assay reagents.

Treatment of electrode surfaces may be advantageous so as to improve or facilitate immobilization, change the wetting properties of the electrode, increase surface area, increase the binding capacity for the immobilization of reagents (e.g., lipid, protein or lipid/protein layers) or the binding of analytes, and/or alter the kinetics of electrochemical reactions at the electrode. In some applications, however, it may be preferable to use untreated electrodes. For example, we have found that it is advantageous to etch carbon ink electrodes prior to immobilization when the application calls for a large dynamic range and therefore a high binding capacity per area of electrode. We have discovered that oxidative etching (e.g., by oxygen plasma) has additional advantages in that the potential for oxidation of tripropyl amine (TPA) and the contact angle for water are both reduced relative to the unetched ink. The low contact angle for water allows reagents to be adsorbed on the electrode by application of the reagents in a small volume of aqueous buffer and allowing the small volume to spread evenly over the electrode surface. Surprisingly, we have found that excellent assays may also be carried out on unetched carbon ink electrodes despite the presence of polymeric binders in the ink. In fact, in some applications requiring high sensitivity or low-non specific binding it is preferred to use unetched carbon ink electrodes so as to minimize the surface area of exposed carbon and therefore minimize background signals and loss of reagents from non-specific binding of reagents to the exposed carbon. Depending on the ink used and the process used to apply the ink, the electrode surface may not be easily wettable by aqueous solutions. We have found that we can compensate for the low wettability of the electrodes during the adsorption of reagents by adding low concentrations of non-ionic detergents to the reagent solutions so as to facilitate the spreading of the solutions over the electrode surface. Even spreading is especially important during the localized immobilization of a reagent from a small volume of solution. For example, we have found that the addition of 0.005-0.04% Triton X-100® allows for the spreading of protein solutions over unetched carbon ink surfaces without affecting the adsorption of the protein to the electrode and without disrupting the ability of a dielectric film applied on or adjacent to the electrode (preferably, a printed dielectric film with a thickness of 0.5-100 micrometers, or more preferably 2-30 micrometers, or most preferably 8-12 micrometers and having a sharply defined edge) to confine fluids to the electrode surface. Preferably, when non-ionic detergents such as Triton X-100 are used to facilitate spreading of reagents (e.g., capture reagents and/or biomembranes) onto unetched screen-printed electrodes (i.e., so as to allow the immobilization of the reagents), the solutions containing the reagents are allowed to dry onto the electrode surface. It has been found that this drying step greatly improves the efficiency and reproducibility of the immobilization process.

Electrodes can be derivatized with chemical functional groups that can be used to attach other materials, such as membranes, to them. Materials may be attached covalently to these functional groups, or they may be adsorbed non-covalently to derivatized or underivatized electrodes. Electrodes may be prepared with chemical functional groups attached covalently to their surface. These chemical functional groups include but are not limited to COOH, OH, $NH_2$, activated carboxyls (e.g., N-hydroxy succinimide (NHS)-esters, poly-(ethylene glycols), thiols, alkyl (($CH_2)_n$) groups, and/or combinations thereof). Certain chemical functional groups (e.g., COOH, OH, $NH_2$, SH, activated carboxyls) may be used to couple reagents to electrodes. For further reference to useful immobilization and bioconjugation techniques see G. Hermanson, A. Mallia and P. Smith, *Immobilized Affinity Ligand Techniques* (Academic Press, San Diego, 1992) and G. Hermanson, *Bioconjugate Techniques* (Academic Press, San Diego, 1996).

In preferred embodiments, NHS-ester groups are used to attach other molecules or materials bearing a nucleophilic chemical functional group (e.g., an amine). In a preferred embodiment, the nucleophilic chemical functional group is present on and/or in a biomolecule, either naturally and/or by chemical derivatization. Examples of suitable biomolecules include, but are not limited to, amino acids, proteins and functional fragments thereof, antibodies, binding fragments of antibodies, enzymes, nucleic acids, and combinations thereof. This is one of many such possible techniques and is generally applicable to the examples given here and many other analogous materials and/or biomolecules. In a preferred embodiment, reagents that may be used for ECL may be attached to the electrode via NHS-ester groups.

In other embodiments of the invention, lipid, protein and/or lipid/protein layers are immobilized via the use of functional groups that self-assemble onto an electrode surface. Phospholipid bilayer membranes (e.g., liposomes) will spontaneously fuse onto the surface of gold electrodes comprising a layer of alkane thiols (or alternatively, lipids presenting thiols in their headgroups) to give lipid monolayers or bilayers (depending on the nature and density of the adsorbed thiol groups). Alternatively, thiols-containing components in a biological membrane may be used to adsorb the biomembrane to a gold surface. Useful functional groups for self-assembly on electrode surfaces include i) thiols, phosphines and isocyanates on soft metal surfaces such as gold and platinum; silanes (e.g., chlorosilanes or alkoxysilanes) on oxide surfaces such as silica and ITO, and carboxylate and phosphonate groups on hard metal surfaces and oxide surfaces such as aluminum and ITO. Phospholipid bilayers can, by themselves, spontaneously assemble (by fusion of vesicles or by Langmuir-Blodgett transfer) on some electrode surfaces to form monolayers (e.g., on hydrophobic surfaces) or bilayers (e.g., on oxide surfaces such a silica or ITO).

It may be desirable to control the extent of non-specific binding of materials to electrodes. Simply by way of non-limiting examples, it may be desirable to reduce or prevent the non-specific adsorption of proteins, antibodies, fragments of antibodies, cells, subcellular particles, viruses, serum and/or one or more of its components, ECL labels (e.g., $Ru^{II}(bpy)_3$ and $Ru^{III}(bpy)_3$ derivatives), oxalates, trialkylamines, antigens, analytes, and/or combinations thereof). In another example, it may be desirable to enhance the binding of biomolecules.

One or more chemical moieties that reduce or prevent non-specific binding (also known as blocking groups) may be present in, on, or in proximity to an electrode. Such moieties, e.g., PEG moieties and/or charged residues (e.g., phosphates, ammonium ions), may be attached to or coated on the electrode. Examples of useful blocking reagents include proteins (e.g., serum albumins and immunoglobins), nucleic acids, polyethylene oxides, polypropylene oxides, block copolymers of polyethylene oxide and polypropylene oxide, polyethylene imines and detergents or surfactants (e.g., classes of non-ionic detergents/surfactants known by the trade names of Brij, Triton, Tween, Thesit, Lubrol, Genapol, Pluronic, Tetronic, F108, and Span). Especially preferred blocking agents for lipid and/or lipid/protein layers include poly cations, preferably poly amines such as poly-lysine or more preferably poly ethylene imine (PEI). These poly cations may be used in combination with protein blockers and/or detergents.

Materials used in electrodes may be treated with surfactants to reduce non-specific binding. For example, electrodes may be treated with surfactants and/or detergents that are well known to one of ordinary skill in the art (for example, the Tween series, Triton, F108, Span, Brij). Solutions of PEGs and/or molecules which behave in similar fashion to PEG (e.g., oligo- or polysaccharides, other hydrophilic oligomers or polymers) ("Polyethylene glycol chemistry: Biotechnical and Biomedical Applications", Harris, J. M. Editor, 1992, Plenum Press) may be used instead of and/or in conjunction with surfactants and/or detergents. Undesirable non-specific adsorption of certain entities such as those listed above may be blocked by competitive non-specific adsorption of a blocking agent, e.g., by a protein such as bovine serum albumin (BSA) or immunoglobulin G (IgG). One may adsorb or covalently attach an assay reagent (e.g., a biomembrane) on an electrode and subsequently treat the electrode with a blocking agent so as to block remaining unoccupied sites on the surface. Alternatively, blocking may be achieved with the unlabeled ligand itself. More specifically, the unlabeled ligand may be immobilized on the unoccupied sites on the surface of the electrode. The unlabeled ligand would be used to block irreversible, non-specific binding. By necessity, such blocking would be followed by extensive washing to liberate the unlabeled ligand from the receptor (the specific, reversible binding side).

In preferred embodiments, it may be desirable to immobilize (by either covalent or non-covalent means) biomolecules or other media to carbon-containing materials, e.g., carbon black, fibrils, and/or carbon dispersed in another material. One may attach antibodies, fragments of antibodies, proteins, enzymes, enzyme substrates, inhibitors, cofactors, antigens, haptens, lipoproteins, liposaccharides, cells, sub-cellular components, cell receptors, viruses, nucleic acids, antigens, lipids, glycoproteins, carbohydrates, peptides, amino acids, hormones, protein-binding ligands, pharmacological agents, and/or combinations thereof. It may also be desirable to attach non-biological entities such as, but not limited to polymers, elastomers, gels, coatings, ECL tags, redox active species (e.g., tripropylamine, oxalates), inorganic materials, chelating agents, linkers, etc. A plurality of species may be co-adsorbed to form a mixed layer on the surface of an electrode.

Electrodes used in the multi-well assay plates of the invention are typically non-porous, however, in some applications it is advantageous to use porous electrodes (e.g., mats of carbon fibers or fibrils, sintered metals, and metals films deposited on filtration membranes, papers or other porous substrates). These applications include those that employ filtration of solutions through the electrode so as to: i) increase mass transport to the electrode surface (e.g., to increase the kinetics of binding of molecules in solution to molecules on the electrode surface); ii) capture particles on the electrode surface; and/or iii) remove liquid from the well.

The assay electrodes, modules and immobilized layers of the invention are useful for carrying out a wide variety of established assay formats, e.g., assays based on the measurement of electrochemical voltage and/or current or, preferably, an electrode-induced luminescence, most preferably, electrochemiluminescence. For examples of methods for conducting ECL assays, the reader is directed to U.S. Pat. Nos. 5,591, 581; 5,641,623; 5,643,713; 5,705,402; 6,066,448; 6,165,708; 6,207,369; and 6,214,552 and Published PCT Applications WO87/06706 and WO98/12539, these references hereby incorporated by reference. Assays may be directed to, but are not limited to, the measurement of the quantity of an analyte; the measurement of a property of a sample (e.g., temperature, luminescence, electrochemical activity, color, turbidity, etc.); the measurement of a chemical, biochemical and/or biological activity (e.g., an enzymatic activity); the measurement of a kinetic or thermodynamic parameter (e.g., the rate or equilibrium constant for a reaction), etc.

In one embodiment of the invention, a sample potentially containing a luminescent, chemiluminescent and/or redox-active substance (preferably an ECL-active substance) is introduced to an assay plate or one or more wells of an assay plate of the invention and an electrochemical or luminescent signal (preferably, electrochemiluminescence) from the sample is induced and measured so as to measure the quantity of the substance and/or identify the substance. In another embodiment of the invention, a sample containing a luminescent, chemiluminescent and/or redox-active substance (preferably an ECL-active substance) is introduced to an assay plate or one or more wells of an assay plate of the invention and an electrochemical or luminescent signal (preferably, electrochemiluminescence) from the sample is induced and measured so as to measure the presence of substances, chemical activities or biological activities that affect the production of the signal from the substance (e.g., the presence, production and/or consumption of ECL coreactants, hydrogen ions, luminescence quenchers, chemiluminescence triggers, etc.). In other embodiments of the invention, luminescent, chemiluminescent and/or redox-active substances (preferably ECL-active substances) are used as labels to allow the monitoring of assay reagents such as enzyme substrates or binding reagents. Assay formats for measuring analytes through the use of labeled binding reagents specific for the analyte include homogeneous and heterogeneous methods. Heterogenous methods may include a wash step to separate labels (and/or labels attached to a material) on a solid phase/electrode from labels in solution.

A wide variety of materials have been shown to emit electrode induced luminescence, particularly electrochemiluminescence, and may be used with the methods, plates, kits, systems and instruments of the invention. In preferred electrochemiluminescence systems, ECL-active materials and/or labels are regenerated after the emission of electrochemiluminescence and, during an electrochemiluminescence experiment, may be repeatedly excited to an excited state and/or induced to emit luminescence. For example, one class of ECL-active materials are believed to function via a mechanism that includes the steps of i) oxidation of the material; ii) reduction of the oxidized material by a strong reducing agent so as to produce the material in an excited state and iii) emission of a photon from the excited state so as to regenerate the ECL-active material. Preferably, the difference in redox potentials between the ECL-active material and the strong reducing agent is sufficient so that the energy released by step (ii) is equal to or greater than the energy of the photon. In an analogous mechanism, steps (i) and (ii) may be replaced by i) reduction of the material and ii) oxidation of the reduced material by a strong oxidizing agent. In some especially preferred systems, the mechanism is believed to further comprise the step of oxidizing an ECL coreactant (e.g., tertiary amines such as tripropyl amine) so as to form the strong reducing agent or, analogously, reducing an ECL coreactant to form the strong oxidizing agent.

Preferred luminescent materials and labels include luminescent organometallic complexes of Ru, Os and Re. Some especially useful materials are polypyridyl complexes of ruthenium and osmium, in particular, complexes having the structure $ML^1L^2L^3$ where M is ruthenium or osmium, and $L^1$, $L^2$ and $L^3$ each are bipyridine, phenanthroline, substituted bipyridine and/or substituted phenanthroline. We have found that the inclusion of substituted bipyridines or phenanthrolines presenting substituents comprising negatively charged groups, preferably sulfate groups and most preferably sulfonate groups (as described in copending U.S. patent application Ser. No. 09/896,974, entitled "ECL Labels Having Improved Non-Specific Binding Properties, Methods of Using and Kits Containing the Same" filed Jun. 29, 2001, the disclosure hereby incorporated by reference) are especially preferred due to their resistance to non-specific binding, in particular to electrodes comprising carbon, carbon particles, carbon fibrils, carbon composites, carbon fibril composites and/or carbon inks.

The invention also relates to detection methods using the electrodes of the present invention.

One aspect of the invention relates to methods of measuring an analyte of interest, the analyte of interest comprising a membrane protein, a membrane lipid, a lipid/protein layer, and/or a biological membrane (or a component thereof), wherein the analyte of interest is immobilized on an electrode (preferably in an assay module, most preferably in the well of a multi-well plate). One embodiment comprises the steps of: i) immobilizing the analyte of interest on an electrode (e.g., by contacting the electrode with a sample comprising the analyte of interest) and ii) measuring the analyte of interest. The immobilization preferably proceeds via the formation of covalent bonds to functional groups on the electrode, or more preferably via the formation of specific binding interactions with binding reagents immobilized on the electrode (e.g., antibodies or lectins, most preferably ConA, WGA, PHA or PWM), or most preferably via passive adsorption on the electrode. The immobilization may involve the formation of a protein/lipid layer comprising the analyte on the electrode or the incorporation of the analyte in a preexisting lipid/protein layer on the electrode surface. The assay method may also comprise the steps of lysing a cell, e.g., to release a cellular analyte into solution, to release an organelle comprising an analyte, and/or to release a membrane fragment comprising the analyte, and, optionally, purifying the released analyte.

Another aspect of the invention relates to methods of measuring an analyte of interest that binds to a biomaterial wherein the biomaterial comprises a membrane protein, a membrane lipid, a lipid/protein layer and/or a biological membrane (or a component thereof) and wherein the biomaterial is immobilized on an electrode (preferably in an assay module, most preferably in the well of a multi-well plate). One embodiment comprises the steps of i) contacting the biomaterial with a sample comprising the analyte; ii) forming a complex on the electrode comprising the analyte and the biomaterial and ii) measuring the analyte of interest. The biomaterial is preferably immobilized on the electrode via covalent bonds to functional groups on the electrode, or more preferably via specific binding interactions with a capture reagent immobilized on the electrode, or most preferably via passive adsorption on the electrode. Optionally, the assay method also comprises the step of immobilizing the biomaterial on the electrode. This immobilization step can be carried out before, during and/or after the step of contacting the biomaterial with the sample.

In one preferred embodiment, a variety of tissue types and/or cell types are immobilized in an array on one or more electrode surfaces, preferably on a carbon electrode, more preferably on a carbon composite electrode, most preferably on a carbon ink electrode. Immobilized cells or tissues may remain viable upon immobilization to the electrode surface. According to this embodiment cells may grow when attached to the surface. Alternatively, the cells or tissues are fixed, cross-linked and/or permeabilized. The assay module may be used for differential tissue/cell typing and for assaying the differences in protein expression and stimulus response for different cell types. The typing may be done in viable cells or after cell lysis.

In another embodiment the whole intact cells or tissues immobilized on the surface are assayed for the activity of the enzymes of interest during the growth phase, or immediately following the immobilization. Alternatively the enzyme activity may be measured after cell lysis.

In one preferred embodiment, the biomaterial immobilized on the electrode surface, preferably on a surface of a carbon electrode, more preferably on a carbon composite electrode, most preferably on a carbon ink electrode, is used to further capture and measure the ligands of interest which interact with the immobilized biomaterial.

Yet according to another embodiment of the invention cells are dispensed into wells containing electrodes having assay domains adapted for measuring one or more cellular components. For example, an assay domain may have a binding reagent that binds a cellular component. Alternatively, when the cellular component is an enzyme, the assay domain may comprise a binding reagent that binds a substrate or product of the enzyme. Similarly, enzymes may be measured using assay domains that comprise enzyme substrates (i.e., by monitoring the transformation of substrate to product). These systems may be used to measure the effect of cell affecting agents (e.g., drugs, hormones, toxins, etc.) or conditions (i.e., changes in temperature, pH, pressure, etc.) on the cells in the wells by challenging the cells with the cell affecting agent or condition and measuring a change in the level of the cell component (e.g., relative to control cells that are not challenged with the agent or condition). The cells may be non-adherent or they may be adherent and allowed to adhere to the electrode surface or other surfaces. In some cases both cells and binding reagents may be immobilized on the same electrode surface. The cells are, optionally, lysed (e.g., by the addition of detergents) or permeabilized prior to measuring the cell components so as to release cell components from within the cells after challenge. We have found that it is possible to carry out electrochemiluminescence based assays in the presence of complex matrices comprising whole cells or cell lysates. In many cases, these assays can be carried out in a non-wash format and do not require the removal of cells and/or cell debris from the wells prior to the ECL measurement. When certain electrode compositions or immobilized reagents are incompatible with cells of interest, the cells or surfaces may be kept separate through the use of a polymer film or membrane deposited on the electrode/surface or suspended between the cells and the electrode/surface. For example, suspended membranes may be provided through in a multi-well format through the use of commercially available membrane inserts (e.g., Millipore Millicel inserts or Costar Transcell inserts).

In another embodiment the external cell membranes can be permeabilized or lysed and the biomaterial specific to a particular organelle (such as Golgi, ER, etc. . . . ) captured on the surface of the electrode (e.g., via the use of specific antibodies). In one example, synaptic vesicles containing α-synuclein are captured and analyzed using LB509 or Syn-1 antibodies. Alternatively, during the early stages of an apoptosis the plasma membrane becomes permeable to small molecules. A labeled substrate can permeate the cell walls and localize on an organelle of interest within the cells; after cell lysis, the organelle is immobilized on the electrode and measured.

In one preferred embodiment, viable cells or tissues are immobilized on the electrode surface and subjected to chemical or biological challenge, such as for example treatment with urea or bacterial infection. Subsequent to challenge, the cellular response on a molecular or morphologic level is measured either through molecular cascade activation, secretion, or expression on the cell surface. Alternatively, cell response may be measured after cells are lysed prior to measurement. In addition, cells may be allowed to grow and replicate in contact with the surface prior to, during, or post challenge. For example, the infection with Staphylococcus Aureus causes a spontaneous cytokine release generally termed as "cytokine storm". The invention provides for immobilizing viable cells on the electrode surface, challenging cells with Staph A and detecting quantities and rate of the specific cytokine release within the "storm".

Alternatively, according to one embodiment, in response to challenge the cytokines may be released from the cell and will activate tyrosine kinases present in solution, which in turn will phosphorylate tyrosine kinase substrates immobilized on the electrode surface. The process may be assayed either after removal of cells, cell debris and non-immobilized biomaterial, or assayed directly using antityrosine antibodies.

Preferably, the aforementioned methods of measuring an analyte further comprise the steps of applying electrical energy (e.g., current or voltage) to the electrode (preferably, under conditions appropriate for inducing electrochemiluminescence, e.g., in the presence of an ECL coreactant such as a tertiary alkylamine, preferably, tripropylamine) and measuring luminescence (preferably, electrochemiluminescence) induced at the electrode (e.g., from a luminescent species, preferably an electrochemiluminescent species, associated with the analyte), wherein the luminescence signal correlates to the amount of analyte present. Optionally, the method may comprise the step of introducing an ECL coreactant prior to the induction of luminescence. The luminescent species may be the analyte itself or it may be a luminescent species linked to the analyte (or to a biomembrane or lipid/protein layer comprising the analyte). Such linkages may include i) a covalent bond (e.g., to the analyte or to a lipid or protein component of a membrane comprising the analyte), ii) a specific binding interaction (e.g., via a labeled antibody directed against the analyte or to a membrane component of a membrane comprising the analyte) and/or iii) a non-specific binding interaction (e.g., using a hydrophobic label that partitions into the lipid bilayer of a membrane comprising the analyte). The assay method, preferably, further comprises the step of forming the linkage between the label and the analyte (or to a component of a membrane comprising the analyte), e.g., by contacting or mixing the analyte with a label or a labeled reagent such as a labeled binding reagent. The formation of the linkage may be carried out before, during and/or after the immobilization step. The assay method may also include one or more wash steps to remove material (e.g., analyte, biomaterial, blocking reagent, labeled reagent, etc.) that is not bound to the electrode.

Another aspect of the invention relates to methods of measuring a binding interaction of a biomaterial with a binding partner, the biomaterial selected from the group consisting of membrane proteins, membrane lipids, lipid/protein layers, biological membranes and components of biological membranes and combinations thereof, wherein the biomaterial is immobilized on an electrode (preferably in an assay module, most preferably in the well of a multi-well plate). One embodiment comprises the steps of i) contacting the biomaterial with a binding partner of the biomaterial; ii) forming a complex on the electrode comprising the biomaterial and the binding partner and ii) measuring the complex so as to measure the binding interaction. The biomaterial is preferably immobilized on the electrode via covalent bonds to functional groups on the electrode, or more preferably via specific binding interactions with a capture reagent immobilized on the electrode, or most preferably via passive adsorption on the electrode. Optionally, the assay method also comprises the step of immobilizing the biomaterial on the electrode. This immobilization step can be carried out before, during and/or after the step of contacting the biomaterial with the binding partner. The measurement of the binding interaction may be used in a variety of applications including, but not limited to, i) measuring the amount of the biomaterial; ii) measuring the amount of the binding partner and iii) measuring the affinity of a biomaterial for the binding partner. The assay method may further comprise the step of contacting the biomaterial and/or the binding partner with an inhibitor of the binding interaction so that the extent of binding is indicative, e.g., of the amount of the inhibitor or the inhibition constant of the inhibitor. The inhibition assay may also be used to screen compounds for inhibitors of the binding interaction.

Preferably, the aforementioned method of measuring a binding interaction further comprise the steps of applying electrical energy (e.g., current or voltage) to the electrode (preferably, under conditions appropriate for inducing electrochemiluminescence, e.g., in the presence of an ECL coreactant) and measuring luminescence (preferably, electrochemiluminescence) induced at the electrode (e.g., from a luminescent species, preferably an electrochemiluminescent species, associated with the binding partner), wherein the luminescence signal correlates to the number of binding interactions. Optionally, the method may comprise the step of introducing an ECL coreactant prior to the induction of luminescence. The luminescent species may be the binding partner itself or it may be a luminescent species linked to the binding partner. Such linkages may include i) a covalent bond, ii) a specific binding interaction (e.g., via a labeled antibody directed against the binding partner) and/or iii) a non-specific binding interaction. The assay method, preferably, further comprises the step of forming the linkage between the label and the binding partner, e.g., by contacting or mixing the binding partner with a label or a labeled reagent such as a labeled binding reagent. The formation of the linkage may be carried out before, during and/or after the immobilization step. The assay method may also include one or more wash steps to remove material (e.g., binding partner, biomaterial, blocking reagent, labeled reagent, etc.) that is not bound to the electrode.

Another aspect of the invention relates to methods of measuring an activity or process that modifies a biological membrane, a membrane protein, and/or a lipid/protein layer, the method comprising the steps of subjecting the biological membrane, a membrane protein, and/or a lipid/protein layer to a sample comprising the activity or to conditions under which the process occurs and measuring the extent of the modification so as to measure the activity or process. The extent of the modification is, preferably, measured by selectively measuring the modified membrane, a membrane protein, and/or a lipid/protein layer and/or the remaining unmodified membranes (or components thereof) according to the assay methods of the invention (e.g., by using labeled antibodies specific for the starting material or product). Optionally, the activity or process is carried out in the presence of an inhibitor of the activity or process so that the extent of modification is indicative, e.g., of the amount of the inhibitor or the inhibition constant of the inhibitor. The inhibition assay may also be used to screen compounds for inhibitors of the binding interaction and/or for measuring an activity or process that modifies a binding partner of the immobilized biological membrane, a membrane protein, and/or a lipid/protein layer.

In one embodiment, a membrane protein, membrane lipid or biological membrane is immobilized on an electrode, subjected to a membrane modifying activity or process, and assayed to determine the extent of modification. In another embodiment, a membrane protein, membrane lipid or biological membrane is subjected to a membrane modifying activity or process, immobilized on an electrode, and assayed to determine the extent of modification. In yet another embodiment, a cell is subjected to a membrane modifying activity or process, the cell is lysed, a biological membrane or membrane component derived from the cell (e.g., an organelle, membrane fragment, membrane vesicle, membrane ghost, membrane protein, membrane lipid, etc) is immobilized on an electrode, and assayed to determine the extent of modification. Examples of activities and processes that can be measured include kinase activity/phosphorylation (including autophosphorylation of membrane bound kinases), phosphatase activity/dephosphorylation, changes in membrane lipid composition or orientation (e.g., changes in phosphatidyl serine levels during apoptosis), hydrolysis or changes in phosphorylation state of membrane phosphatidyl inositols, prenylation of proteins, binding and/or release of soluble proteins and/or peripheral membrane proteins to biological membranes, transfer of proteins and/or lipids between biological membranes (e.g., between organelles and/or between an organelle and the cytoplasmic membrane), etc.

One embodiment of the method of measuring an activity or process (or, alternatively, an inhibitor of an activity or process) that modifies a biological membrane relates to measuring an activity or process that results from the activation of a membrane protein (e.g., as a result of a change in the physical or chemical environment, a change in membrane potential, the aggregation of the protein, the binding of a ligand to a membrane receptor, etc.). For example, the activation of a membrane protein may lead to phosphorylation of the protein or of other components of the membrane (the phosphorylated components being measured, e.g., using phosphopeptide specific antibodies); ii) the sequestration or binding (or, alternatively, the release) to the membrane of soluble cellular components such as peripheral membrane proteins or cytoplasmic proteins (the binding of soluble cellular components being measured, e.g., using antibodies specific for the components); iii) the up or down regulation of membrane proteins (the membrane proteins being measured, e.g., using antibodies specific for the specific membrane protein being monitored), etc.

The invention is also directed to methods for improving biomaterial capture.

Stable adsorption of biomaterials of interest onto a surface typically requires chemical modification of the surface which results in a covalent linkage between the surface and the biomaterial or alternatively the covalent linkage to one of the components of a specific binding pair, e.g. biotin—streptavidin, which modulates surface binding. Surprisingly the passive adsorption of biomaterials, including membrane fragments and vesicles, to an electrode surface has worked extremely well. The invention also provides alternatives for biomaterials which resist passive capture, or that are highly dependent on membrane properties, such as fluidity or microphase separation.

In one embodiment of the present invention the biomaterials are immobilized via lectin-modulated capture. Advantageously, lectin-mediated capture does not require specific modification of the many biomaterials of interest and, generally, does not disrupt the activity of the biomaterial of interest as depicted. The lectins of the instant invention preferably include PHA, WGA, ConA and PWM ("the preferred lectins"), which are readily adsorbed on surfaces. PHA and, in particular, PWM have been found to be especially efficient at immobilizing a variety of biological membrane fragments. The lectins may be immobilized on glass, plastic (e.g., polystyrene, polypropylene, pvc, etc.). In certain embodiments of the invention, the lectins are immobilized in the wells of a multi-well plate for use in ELISA, fluorescence, chemiluminescence, phosphorescence, or radioactivity based assays. Alternatively, the lectins may be immobilized on microparticles, preferably magnatizable microparticles. Such microparticles may be used as solid phase supports for a variety of assay formats including ECL assays (see, e.g., U.S. Pat. No. 6,325,973).

Preferably the lectins are immobilized on the surface of a sensing means, more preferably an electrode. In one specific embodiment of the instant invention lectins can be immobilized on a carbon surface (preferably, a composite containing elemental carbon, most preferably a surface formed from a carbon ink) either passively, or through biotin-avidin mediated interaction and used further for biomaterial capture. One preferred embodiment involves passive incubation (i.e., contacting unmodified lectins with a surface under normal experimental conditions). For example, in one specific embodiment the incubation at 4° C. for one hour is sufficient to immobilize the desired amount of the lectin on the surface. Optionally, the surface may be blocked with blocking agents such as proteins (e.g., bovine serum albumin) or detergents (e.g., non-ionic detergents such as Thesit, Tween 20, Triton X-100 and the like). Especially preferred blocking agents are poly cations, preferably poly amines such as poly-lysine or more preferably poly ethylene imine (PEI). These poly cations may be used in combination with protein blockers and/or detergents. The surface having lectins adsorbed thereon can be stored dry and rehydrated at a desired later time.

In one specific embodiment, the excess of non-adsorbed lectins, such as PHA, WGA, ConA or PWM is removed prior to contacting the surface with the biomaterial of interest. According to another specific embodiment of the present invention, excess non-immobilized biomaterial is removed after incubating the lectin-treated surface with the biomaterial of interest for a desired period of time.

In one preferred embodiment of the present invention, the surface is pre-treated with cleaning reagents, preferably detergents, denaturants, high pH buffer solutions or enzymes, prior to adsorbing the lectins, preferably adsorbing PHA, WGA, ConA or PWM. In another preferred embodiment of the present invention, the surface is blocked with one or more blocking reagents after removing the excess of non-immobilized biomaterial.

In one specific embodiment of the present invention the surface is a surface of an electrode, preferably a carbon electrode, more preferably a patterned carbon electrode. According to this embodiment, lectins, preferably PHA, WGA, ConA and PWM ("the preferred lectins"), most preferably PWM or PHA, are directly pre-adsorbed onto a surface, preferably the surface of a sensing means, more preferably an electrode, most preferably a surface comprising elemental carbon. Optionally, the surfaces are plasma treated so as to increase the surface capacity of the surface for binding or to expose components of a composite (e.g., to expose carbon in a carbon composite such as a carbon ink). According to one preferred embodiment of the instant invention the direct adsorption of the lectins of the instant invention does not involve carbon surface derivatization and provides significant improvement in speed and ease of use. Alternatively, according to one specific embodiment of the instant invention biotinylated lectins are readily immobilized on an avidin coated carbon surface.

According to the present invention, the lectins advantageously retain their activity, namely the ability to interact with, bind and capture the biomaterial of interest after being immobilized on the surface. For example, PHA remains active on a surface even after the surface has been dried up for 24 hours, preferably after one week, more preferably after one year. According to the instant invention the pre-treated surface may be used immediately, or stored and used at a convenient time to capture the biomaterial of interest.

The high affinity of the preferred lectins of the present invention for their respective polysaccharides is one of the advantageous characteristics of the instant invention. Features of the specific oligosaccharide moieties recognized by some of the preferred lectins have been studied, e.g., PWM in Yokoyama, K. et al., *Biochimica et Biophysica Acta,* 538 (1978) 384-396, and WGA in Katagiri, Y. et al., *Carbohydrate Research,* 120 (1983) 283-292. Such information can be applied to determine the applicability of specific lectins for capture of specific biomaterials. For example, PWM and PHA lectins successfully capture diverse biomaterial types tested in the instant invention, e.g. microsomes (membrane fragments) derived from K562, A431 and HEK-293 cells.

While the current understanding of the mechanism of this process is in no way expected to limit the scope of the claimed subject matter, it is accepted in the art that lectins capture biomaterial through specific binding to oligosaccharides displayed on the surface of the biomaterial of interest (FIG. 1E). The preferred biomaterial of interest immobilized using the invention is selected from the group consisting of glycosylated proteins, lipid-binding proteins, membrane proteins, lipid/protein layers, microsomal extracts, cell-extracted lipid vesicles, membrane lipids, intact cell, cell lysate, cell fragment, cell membrane, membrane ghost, organelle, organelle fragment, organelle membrane, virion, virion fragment, virion membrane, liposome, detergent solubilized protein, detergent solubilized lipid, whole cells, tissues and combinations thereof.

In one preferred embodiment, the captured biomaterial comprises receptors, preferably membrane receptors, which remain active upon surface immobilization. The isolated receptor can either be immobilized alone or as a part of a larger complex and/or embedded into the membrane.

One embodiment the instant invention provides methods to capture a biomaterial of interest on a surface (preferably a surface comprising elemental carbon, more preferably the surface of the carbon-containing electrode) having preadsorbed antibodies specific to the biomaterial of interest. These antibodies may be used alone or in combinations with lectins, such as the preferred lectins on the instant invention. In one specific embodiment of the instant invention, the antibodies are used to sub-fractionate the microsomal pool to specifically enhance the ratio of microsomes containing biomaterial of interest to total microsomes in a sample for microsomes captured on the carbon surface.

According to one specific embodiment of the present invention, the antibodies may be preadsorbed on the surface by passive incubation. Alternatively, biotinylated antibodies may be immobilized on an avidin or streptavidin coated surface through biotin-avidin, or biotin-streptavidin interaction.

In one embodiment of the invention, the lipid and/or lipid protein layers are on a particulate solid phase such as magnetic particles (e.g., polystyrene particles having a core that comprises iron oxide nanoparticles). Such immobilization can be achieved by passive adsorption, covalent attachment, via bio-specific interactions, etc. as described above. Such immobilized lipid and/or lipid/protein layers can be used in electrode induced luminescence assays in a fashion analogous to layers immobilized on an electrode by including in the method the step of collecting the magnetic particles on an electrode (e.g., by attracting magnetic particles to the surface of an electrode by applying a magnetic field adjacent to the electrode).

5.6 Kits

Another aspect of the invention relates to kits for use in conducting assays, preferably luminescence assays, more preferably electrode induced luminescence assays, and most preferably electrochemiluminescence assays, comprising one or more of the assay electrodes and/or assay modules of the invention and at least one assay component selected from the group consisting of: (a) at least one luminescent label (preferably electrochemiluminescent label); (b) at least one electrochemiluminescence coreactant; (c) one or more binding reagents; (d) a pH buffer; (e) one or more blocking reagents; (f) preservatives; (g) stabilizing agents; (h) enzymes; (i) detergents; (j) desiccants and (k) hygroscopic agents.

Preferably, the kit comprises the assay module having one or more assay electrodes, preferably an assay plate, more preferably multi-well assay plates and the assay component (s) in one or more, preferably two or more, more preferably three or more containers.

Preferably, the assay module is a multi-well plate adapted for use in conducting the electrode induced luminescence assays (preferably electrochemiluminescence assays) in sectors.

According to one embodiment, the kit comprises one or more of the assay components in one or more plate wells, preferably in dry form.

According to one embodiment, the assay components are in separate containers. According to another embodiment, the kit includes a container comprising binding reagents and stabilizing agents. According to another embodiment, the well reagents may include binding reagents, stabilizing agents. Preferably, the kits do not contain any liquids in the wells.

One preferred embodiment relates to a kit for use in conducting electrode induced luminescence assays (preferably electrochemiluminescence assays) comprising an assay plate, preferably a multi-well assay plate, and at least one assay component selected from the group consisting of at least one luminescent label (preferably electrochemiluminescent label) and at least one electrochemiluminescence coreactant).

Another preferred embodiment the invention relates to a kit for preparing a surface for immobilization of a biomaterial. The kit components are conveniently designed to provide reagents to improve surface ability to immobilize biomaterial by pre-treating the surface of interest with lectins, cell-adhesion reagents or antibodies according to the invention.

Another embodiment relates to a kit comprising a multi-well plate and at least one electrode induced luminescent label (preferably electrochemiluminescent label) and/or at least one bioreagent and/or at least one blocking reagent (e.g., BSA). Yet another preferred embodiment the invention relates to a multi-well plate wherein at least one well comprises a surface treated with lectins, preferably PHA, WGA, ConA or PWM. In one preferred embodiment, the multi-well plate further comprises a biomaterial of interest immobilized in at least one well through lectin-modulated capture. In one specific embodiment of the present invention at least one surface of the well is an electrode, preferably carbon electrode, more preferably patterned carbon electrode.

According to one preferred embodiment, the kit comprises at least one material selected from group consisting of intact cell, cell lysate, cell fragment, cell membrane, membrane ghost, organelle, organelle fragment, organelle membrane, virion, virion fragment, virion membrane, liposome, detergent solubilized protein, detergent solubilized lipid or combinations thereof.

According to another embodiment, the kit comprises a biomaterial selected from the group consisting of plasma membrane fragments, endosomes, clathrin-coated vesicles, endoplamic reticulum fragments, synaptic vesicles, golgi fragments, membrane subdomains, mitochondria, peroxisomes, lysosomes, liposomes, viral particles, viral-induced membrane enclosed particles shed from cells, and intact, organismally-derived lipid membrane bodies.

According to one preferred embodiment, the kit comprises at least one bioreagent, preferably immobilized on the plate surface selected from: antibodies, fragments of antibodies, proteins, enzymes, enzyme substrates, inhibitors, cofactors, antigens, haptens, lipoproteins, liposaccharides, cells, subcellular components, cell receptors, viruses, nucleic acids, antigens, lipids, glycoproteins, carbohydrates, peptides, amino acids, hormones, protein-binding ligands, pharmacological agents, luminescent labels (preferably ECL labels) or combinations thereof. Preferably, at least one bioreagent is adapted or selected for binding to one or more membranes resulting in an electrode having such immobilized membranes.

Preferably, the biomaterial comprises a lipid/protein layer which contains at least one active protein selected from the group consisting of: single transmembrane receptors with intrinsic tyrosine kinase activity; non-tyrosine kinase transmembrane receptors (e.g., transferrin receptor); G-protein coupled receptors (GPCR); GPCR effector proteins (e.g., adenylate cyclase); phosphoinositides (e.g., phosphatidy inositol 4,5 bisphosphate ($PIP_2$)); phospholipid or sphingolipid composition, identification, or function (i.e., changes in phosphotidylserine presence during apoptosis); organelle-bound GTPases/guanine nucleotide exchange factors (GEFs)/GTPase activating proteins (GAPs); cytokine/chemokine receptors; cell adhesion molecules (e.g., VCAM, integrins); cytoplasmic peripheral membrane protein kinases (e.g., src); intracellular protein kinase adaptor/docking proteins (e.g., insulin receptor substrate 1, GRB2); ion channels (e.g., nicotinic acetylcholine receptor, CFTR, etc.); passive transporters (e.g., glucose); active (ATP-driven) transporters; ion-linked transporters (e.g., Na+/glucose); glycosyltranferases/glycoprotein modifying enzymes; nuclear membrane fragments; and soluble receptors.

Preferably, the kit includes immobilized reagents that comprise proteins, nucleic acids, or combinations thereof.

According to one preferred embodiment, the plurality of wells includes at least two different bioreagents. For example, a well may include two or more assay domains, wherein two or more assay domains have different bioreagents.

Preferably, the kit comprises at least one electrochemiluminescence coreactant and/or at least one electrode induced luminescence label (preferably electrochemiluminescent label).

According to another embodiment, the kit is adapted for multiple assays. Preferably, the kit further comprises an additional assay reagent for use in an additional assay, the additional assay selected from the group consisting of radioactive assays, enzyme assays, chemical colorimetric assays, fluorescence assays, chemiluminescence assays and combinations thereof.

According to another embodiment, the kit comprises two or more, preferably four or more, more preferably eight or more, more preferably 15 or more and most preferably 25 or more assay modules or plates. According to a preferred embodiment, the kit is contained in a resealable bag or container (e.g., zip-lock opening).

Preferably, the bag or container is substantially impermeable to water. According to one preferred embodiment, the bag is a foil, preferably an aluminized foil.

The packaging may be translucent, transparent or opaque. Preferably, the plates are packaged in aluminum lined plastic containers or bags containing a dry or inert atmosphere (e.g., the bags may be sealed under an atmosphere of nitrogen or argon or the bags may contain a dessicant). According to another embodiment, the containers are vacuum sealed.

Preferably, the container contains 1 plate. According to another embodiment, the container contains ten plates. According to another embodiment, the container includes between 10 and 100 plates.

Preferably, the assay modules or plates are sterile and/or substantially free of dust and other contaminants.

Preferably, the assay modules are also substantially sterile.

Another embodiment relates to an assay precursor module comprising at least one electrode and at least one binding reagent immobilized on said electrode, said binding reagent capable of specifically binding with one or more biomaterials selected from the group consisting of lipid proteins, lipid/protein layers and/or membrane lipids thereby forming an assay module having said one or more biomaterials immobilized on said electrode. Preferably, one or more biomaterials comprise natural lipid bilayers. According to a preferred embodiment, at least one binding reagent is capable of specifically binding with a biomaterials derived from or selected from the group consisting of cells, cell fragments, cell membranes, organelle, cell nuclei or combinations thereof. One embodiment relates to an assay precursor module comprising a plurality of electrodes, said electrodes having at least one binding reagent immobilized thereon, said binding reagents capable of specifically binding with one or more lipid proteins, one or more lipid/protein layers, and/or one or more membrane lipids.

5.11 Method of Selecting Biologically Active Compounds and Producing Novel Drugs Another aspect of the invention relates to improved methods and systems for selecting or identifying biologically active compounds and, optionally, incorporating such biologically active compounds into suitable carrier compositions in appropriate dosages. The invention includes the use of the assay electrodes, kits and/or methods of the invention to screen for new drugs, preferably, by high-throughput screening (HTS), preferably involving screening of greater than 50, more preferably 100, more preferably 500, even more preferably 1,000, and most preferably 5,000. According to a particularly preferred embodiment, the screening involves greater than 10,000, greater than 50,000, greater than 100,000, greater than 500,000 and/or greater than 1,000,000 compounds.

One embodiment of the invention relates to a method for selecting or identifying biologically active compounds from a library of compounds, said method comprising screening said library of compounds for biological or biochemical activity, wherein said screening includes assaying the library of compounds for the biological or biochemical activity, the assays being conducted using the assay electrodes of the invention.

Preferably, the method further comprises identifying one or more active compounds.

Preferably, the method further comprises testing said one or more active compounds for bioavailability, toxicity and/or biological activity in vivo. According to one preferred embodiment, the testing comprises further screening using the assay electrodes of the invention.

Preferably, the method further comprises synthesizing analogues of said one or more active compounds. According to one preferred embodiment, the analogues are screened for bioavailability, biological activity and/or toxicity using the assay electrodes of the invention.

According to a particularly preferred embodiment, the method further comprises formulating the one or more compounds into drugs for administrating to humans and/or animals. Preferably, the formulating comprises determining the suitable amount of the one or more active compounds in the drug and mixing the suitable amount with one or excipients or carriers. Preferably, the excepient comprises sugar and/or starch.

Another embodiment of the invention relates to a method of analyzing one or more complex mixtures of biochemical substances to measure a plurality of binding components therein, comprising:
 (a) contacting said mixtures with one or more assay electrodes having one or more lipid/protein layers immobilized thereon, preferably by adding said mixtures to a multi-well plate adapted for electrode induced luminescence assays (preferably electrochemiluminescence assays), wherein the wells of the plate include the assay electrodes;
 (b) applying a voltage or current to the electrodes sufficient to induce luminesce; and
 (c) measuring emitted luminescence.

Another embodiment of the invention relates to a method of analyzing the output of one or more combinatorial (biological and/or chemical) mixtures to measure a plurality of binding components therein, comprising:
 (a) contacting said mixtures to one or more assay electrodes, preferably by introducing said mixture into a multi-well plate adapted for electrode induced luminescence (preferably electrochemiluminescence) assays, said plate having a plurality of wells comprising a one or more assay electrodes;
 (b) applying a voltage or current to the electrodes sufficient to induce luminesce; and
 (c) measuring emitted luminescence.

Another embodiment of the invention relates to a method for measuring a single biochemical substance in a sample in a multiplicity of simultaneous assays, comprising:
 (a) contacting said sample with an assay electrode, preferably by introducing said sample into a multi-well plate adapted for electrode induced luminescence (preferably electrochemiluminescence) assays, said plate having a plurality of wells comprising a one or more assay electrodes;
 (b) applying a voltage or current to the electrodes sufficient to induce luminesce; and
 (c) measuring emitted luminescence.

A further embodiment of the invention relates to a method of drug discovery comprising:
 (a) selecting a multiplicity of compounds for testing;
 (b) screening said multiplicity of compounds for biological activity (using any one of the multi-well plates and/or apparatus described above) to find one or more biologically active compounds; and
 (c) modifying said one or more biologically active compounds to reduce toxicity and/or enhance biological activity thereby forming one or more modified biologically active compounds.

Preferably, the method further comprises screening said modified biologically active compounds for biological activity and/or toxicity (using the assay electrodes of the invention described above).

Preferably, the method further comprises determining the appropriate dosage of one or more of said modified biologically active compounds. Preferably, the method still further comprises incorporating such dosage into a suitable carrier such as sugar or starch to form a drug in solid (e.g., pill or tablet) or liquid form.

Advantageously, the assay electrodes, assay modules and methods of the invention may be integrated into and/or used in a variety of screening and/or drug discovery methods. Such screening and/or drug discovery methods include those set forth in U.S. Pat. No. 5,565,325 to Blake; U.S. Pat. No. 5,593,135 to Chen et al.; U.S. Pat. No. 5,521,135 to Thastrup et al.; U.S. Pat. No. 5,684,711 to Agrafiotis et al.; U.S. Pat. No. 5,639,603 to Dower et al.; U.S. Pat. No. 5,569,588 to Ashby et al.; U.S. Pat. No. 5,541,061; U.S. Pat. No. 5,574,656; and U.S. Pat. No. 5,783,431 to Peterson et al.

According to another embodiment, the invention further comprises identifying adverse effects associated with the drug and storing information relating to the adverse effects in a database. See, U.S. Pat. No. 6,219,674 by Classen, hereby incorporated by reference.

Another aspect of the invention relates to improved biologically active compounds and/or drugs made using the inventive methods.

6. EXAMPLES

The following examples are illustrative of some of products and methods falling within the scope of the present invention. They are, of course, not to be considered in any way limitative of the invention. Numerous changes and modification can be made with respect to the invention by one of ordinary skill in the art without undue experimentation.
Materials and Methods.

Compound 1 pictured below (Sulfo-TAG NHS Ester, Meso Scale Diagnostics) is the NHS ester of an electrochemiluminescent label used to label biomolecules for electrochemiluminescence measurements. Labeling of biomolecules was carried out by adding Sulfo-TAG NHS Ester to a solution of the biomolecule in phosphate buffered saline, pH 8.0. The labeled biomolecules were typically purified from unbound label by size exclusion chromatography (using, e.g., Superdex Peptide Gel of Sephadex G50, Pharmacia Biosciences) or reverse phase HPLC. For labeled proteins, the ratio of labels per protein was calculated from the concentration of labels (calculated from the extinction coefficient of Sulfo-TAG at 455 nm, $\epsilon_{455}$~13,700 $M^-cm^{-1}$) and the concentration of protein (determined using the BCA Protein Assay, Pierce Chemicals). Lectins and biotinylated lectins were purchased from EY Labs, or Vector Labs.

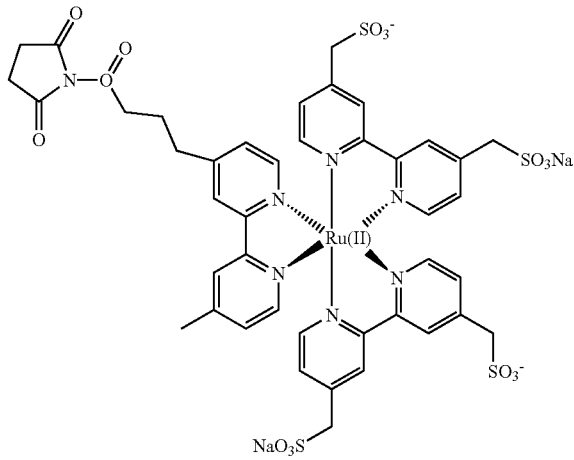

Electrochemiluminescence measurements were carried out using screen-printed carbon ink electrodes patterned on the bottom of specially designed 96-well multi-well plates. The plates are described in more detail in copending Application No. 60/301,932 (entitled "Assay Plates, Reader Systems and Methods for Luminescence Test Measurements", filed on Jun. 29, 2001, hereby incorporated by reference) and particularly in the description of Plate Type B in Example 6.1. Analogous plates are now commercially available (MSD Multi-Array Plates, Meso Scale Discovery). Each well of the plate had a working electrode (roughly in the center of the well) and two counter electrodes (roughly at two edges of the well). In some examples, the carbon ink electrodes were treated with an oxygen plasma to increase the surface area of exposed carbon particles and to improve the wettability of the surface (plasma treatment was not required for carrying out the assays, however plasma treatment was found to improve the ratio of signal to background as well as assay precision). The exposed working electrode surface in each well was defined by a surrounding printed dielectric ink layer that could be used to confine small volumes of fluid to the working electrode.

Electrochemiluminescence from ECL labels on the surface of the carbon electrodes was induced and measured using an imaging plate reader as described in Example 6.3 of copending Provisional Application No. 60/301,932 (entitled "Assay Plates, Reader Systems and Methods for Luminescence Test Measurements", filed on Jun. 29, 2001, hereby incorporated by reference). Analogous plate readers are now commercially available (Sector HTS instrument, Meso Scale Discovery).

Example 1

EGF-EGF Receptor Binding Assays

This example shows an electrochemiluminescence-based assay measuring the binding of epidermal growth factor (EGF) to immobilized membrane fragments containing the epidermal growth factor receptor (EGFR). This example also shows an electrochemiluminescence-based assay measuring the binding of epidermal growth factor (EGF) to immobilized whole viable cells containing EGFR.

EGFR is a member of the receptor tyrosine kinase family of cellular receptors. It is an integral membrane protein that consists of an extra-cellular domain with EGF binding activity, a trans-membrane domain and a cytoplasmic domain with tyrosine kinase activity. The receptor is found in the plasma membranes of a variety of cell types including many epithelial and fibroblastic cell lines. EGFR signaling is involved in a wide array of cellular processes including differentiation, apoptosis, protein secretion, and enhanced cell motility. It is also a target for drug development efforts directed towards developing new agents for treating cancer and for aiding wound repair.

The EGF-EGFR binding assay uses immobilized EGFR-containing membrane fragments that are immobilized on the surface of a carbon ink electrode by passive adsorption or through a bio-specific interaction. Alternatively, whole EGFR-containing cells may be immobilized on the electrode. The binding of labeled EGF to the immobilized EGFR is measured through the electrochemiluminescence detection of an electrochemiluminescent label linked to the EGF. The assay scheme is outlined for the case of passively adsorbed membranes in FIG. 2 and is described in more detail below. It should be noted that, while shown as spherical vesicles, the vesicles shown in FIG. 2 may also include bilayer or monolayer sheets or be bilayer or monolayer sheets (instead of or in addition to vesicles), e.g., as shown in FIGS. 1B, 1C and 1D. Also, the assay may be performed using electrodes coated with capture reagents, such as lectins or antibodies, as outlined in FIG. 1E. The assay can be used to measure EGF or EGFR or to measure or screen for substances (e.g., inhibitors or promoters) that influence the binding of EGF to EGFR. While this example describes a binding assay for binding of ligands to the EGFR, the techniques described in this example are broadly applicable to other membrane-associated proteins, in particular, other receptor tyrosine kinases.

Example 1.1

Labeling of EGF

EGF was labeled with Sulfo-TAG NHS Ester. The product hereafter is referred to as STAG-EGF had approximately two labels per protein molecule.

Example 1.2

Preparation of EGFR-Containing Membrane Fragments

EGFR-containing membrane fragments were prepared from A-431 cells, an adherent human epidermoid carcinoma cell line that expresses ~$10^6$ EGFR per cell. As a negative control, membrane fragments were prepared, by an analogous method, from K-562 cells, a human cell line (isolated from a patient with chronic myelogenous leukemia) that does not express EGFR. Both cell lines are available from the American Type Culture Collection (Manassas, Va.).

The A-431 cells were grown in Dulbecco's Modified Eagle Medium (DMEM) containing 10% (v/v) fetal calf serum to 70-80% confluence in 150 mm petri dishes. Prior to processing, the cells were allowed to grow overnight in the same media but having a reduced concentration of fetal calf serum −5% (v/v). The cells were washed with cold D-PBS (Dulbecco's Phosphate Buffered Saline, GIBCO #14040-133). To each dish was added 1 mL of cold HE Buffer, a buffer containing 20 mM HEPES, 1 mM EDTA, pH 8.0 and also containing a cocktail of protease inhibitors (Complete Mini EDTA-Free Protease Cocktail Tablets, Roche Molecular Biochemicals, 1 tablet per 10 mL of buffer). The cells were scraped off the surface of the petri dishes. The cells in the resultant suspension were lysed with a Dounce Homogenizer (25 strokes with a loose-fitting piston and 25 strokes with a tight fitting piston). The cell lysate was centrifuged (1200 rpm, 5 min, 4° C.) to remove intact cells and large cellular debris. The supernatant was centrifuged at a higher speed (9000 rpm, 30 min, 4° C.) to pellet the cell membrane fragments. The pellet was resuspended in HE Buffer (1 mL for 8 petri dishes of cells) and the suspension was passed gently through a 26 or 28 G needle (the flat side of the needle held against the wall of a plastic tube). This process was repeated 15 times (this additional shear homogenation step was found to improve the reproducibility of assays using the membrane fragments, presumably, by breaking up aggregates and making the membrane fragments more uniform in size).

The resultant suspension was assayed for total protein content using the BCA Assay (Pierce Chemical Co.) and diluted, if necessary, to a protein concentration of between 1.0 and 1.6 mg/mL. Optionally, the membrane fragments could be further purified, e.g., by centrifugation through a sucrose gradient, however, additional purification steps had little if any effect on assays using the fragments. The membrane suspensions were flash frozen in a dry ice/ethanol bath and stored at −80° C. The structure of the membrane fragments was not characterized but is believed to consist primarily of membrane vesicles and probably includes both vesicles oriented to present the extra-cellular side of the cell membrane and vesicles oriented to present the cytoplasmic side of the cell membrane and possibly membrane sheets (e.g., planar bilayers as opposed to closed spherical structures).

Example 1.3.1

Passive Adsorption of Membrane Fragments on Carbon Ink Electrodes

Membrane fragments were immobilized by passive adsorption on plasma treated screen-printed carbon ink electrodes patterned on the bottom of the specially designed 96-well multi-well plates described above.

Figure 2:
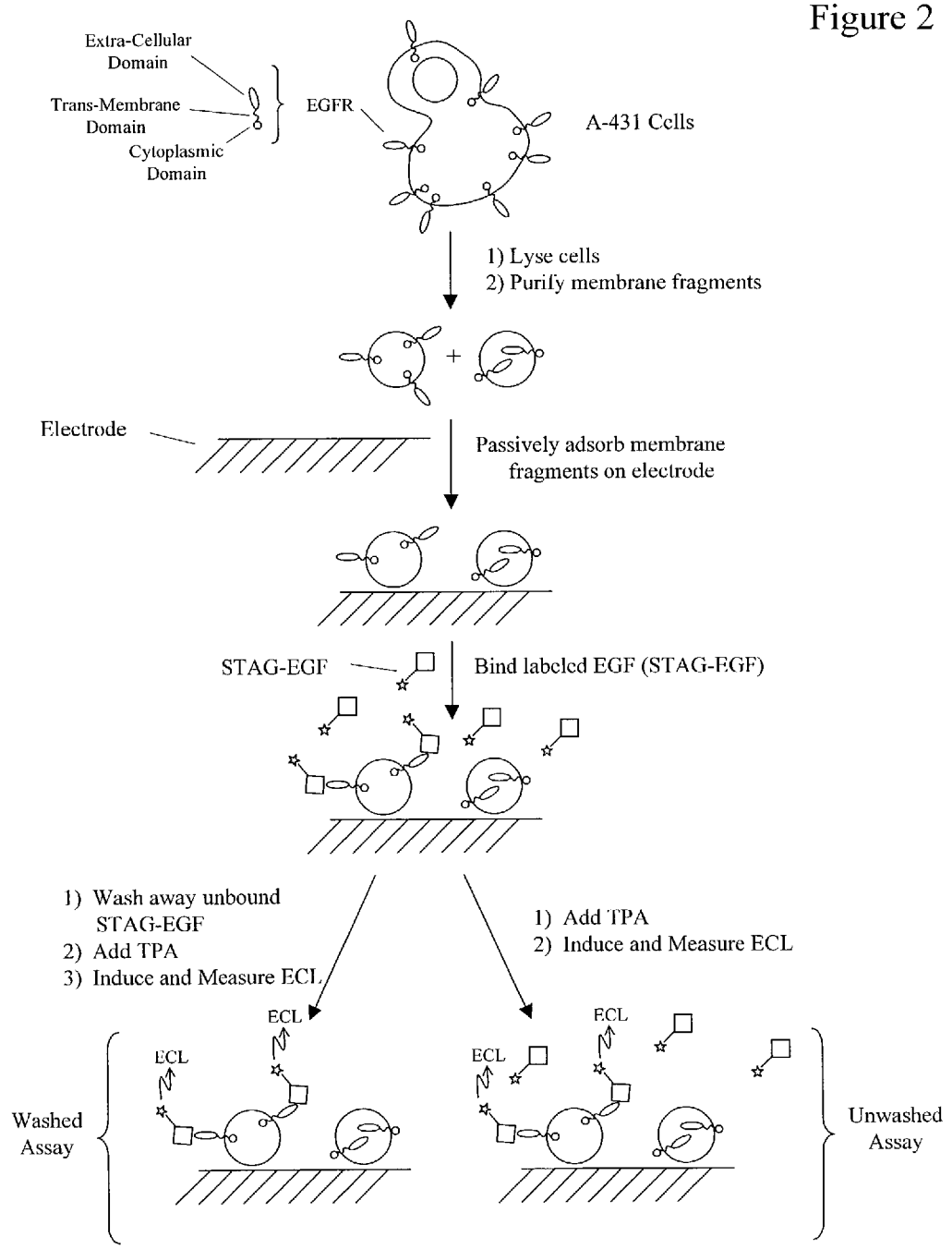
FIG. 2 is a schematic representation of the immobilization and detection of biological membrane fragments onto an assay surface according to one embodiment of the invention.

Frozen suspensions of membrane fragments were allowed to thaw slowly on ice. The suspensions were then diluted in 0.1 M sodium carbonate buffer, pH 9.0 (or, alternatively, Phosphate Buffered Saline) to give a protein concentration of 0.1 mg/mL. The suspensions (5 µL/well, ~1000 cell equivalents) were applied to the working electrodes in the wells of the multi-well plate and incubated for 15-60 min so as to allow the membrane fragments to passively adsorb onto the electrode surfaces. Under these conditions, the suspension was confined to the exposed surface of the working electrode (having a geometric surface area of 0.21 cm$^2$) by the dielectric layer, thereby preventing the adsorption of the membranes to other surfaces. The amount of membrane fragments was optimized for the working electrode area used so as to maximize the amount of active receptor on the electrode while minimizing the amount of non-immobilized or weakly immobilized membrane fragments. The structure of the adsorbed membrane fragments was not characterized but may include: i) adsorbed intact membrane vesicles (as depicted in FIG. 2); ii) vesicles that opened on adsorption to give electrode surfaces coated with phospholipid monolayers, bilayers or multilayers (the membrane proteins being associated with the phospholipid layer and/or iii) membrane proteins that are directly adsorbed on the electrode surface.

The treated plates were immediately used "as is" (i.e., without washing) in the EGF binding assay. Optionally, the plates were stored dry and used at a later time. In one example, the well bottoms were flooded with 25 uL of phosphate buffered saline, pH 7.4 (PBS) and stored in this wet state without degradation in performance. Alternatively, the plates could be blocked prior to use with blocking agents (e.g., proteins such as bovine serum albumin (BSA) or non-ionic detergents such as Thesit) designed to block uncoated surfaces in the well. Surprisingly, exposure of the immobilized membranes, during blocking or during the course of an assay, to non-ionic detergents such as Thesit (e.g., at concentrations up to 0.02%) and Triton X-100 (e.g., at concentrations as high as 0.2%) had only small effects on assay signals, despite the known ability of these detergents to lyse cell membranes and solubilize membrane proteins. Even more remarkably, it was found that the plates could be stored dry (e.g., by allowing the membrane suspension to dry on the working electrode during the immobilization step). In fact, assays conducted by rehydrating dried plates gave higher signals in EGF binding assays (presumably because the drying process opened up and/or reoriented immobilized membrane fragments so as to expose additional ligand binding sites).

Example 1.3.2

Immobilization of Membrane Fragments Utilizing Lectins Directly Preadsorbed on Carbon Ink Electrodes The working electrodes of plasma treated MultiArray 96-well plates (Meso Scale Discovery) were treated with 10 uL of solutions containing 4.0 µM ConA, 1.0 µM PHA-E or 4.0 µM WGA in PBS. The plate was sealed and incubated for 1 h with intermittent shaking. Following the incubation, the lectin solution was discarded and the plate was washed four times with PBS. Following the PBS wash, 25 µL of the 0.06 µg/µl A431 or K562 membrane solutions in PBS (prepared as described in the Example 1.2) were added to the wells (total 1.5 µg per well) as described in Example 1.3.1. The plates were sealed and incubated for one hour at room temperature. The liquid in the wells was removed and the plates were used in the STAG-EGF binding assay.

Example 1.3.3

Immobilization of Membrane Fragments Utilizing Biotin-Labeled Lectins Preadsorbed on Avidin-Coated Carbon Ink Electrodes Plasma treated Multi-Array plates having avidin-coated working electrodes (Meso Scale Discovery) were blocked with 3% BSA and washed with PBS. The electrodes were coated with biotinylated lectins by adding 25 µl per well of 190 nM Con-Ab, 190 nM PHA-Eb or 380 nM WGAb in PBS. The plate was sealed and incubated for 1 h with intermittent shaking. Following the incubation, the lectin solution was discarded and the lectin coated electrodes were treated with membrane fragments as describe in Example 1.3.2. The plates were then used in the STAG-EGF binding assay.

Example 1.3.4

Antibody Assisted Immobilization of Membrane Fragments on Carbon Ink Electrodes Plasma treated Multi-Array plates having avidin-coated working electrodes (Meso Scale Discovery) were blocked with 3% BSA solution and washed with PBS. The electrodes were coated with anti-EGFR antibodies by adding 25 μL (or 1 pmol) of a biotinylated anti-EGFR antibody (mouse anti-EGFR clone 199.12 from NeoMarkers) in PBS plus 1% BSA per well. Following the incubation, the antibody solution was discarded and the plate was washed four times with PBS. Membranes fragments prepared as described in Example 1.2 were added at 10 μL (0.50 μg) per well. Plates were sealed and incubated for one hour at room temperature. The excess of the non-adsorbed material was discarded and the plates used in the STAG-EGF binding assay.

Example 1.3.5

Cell Immobilization on the Electrode Surface

A-431 cells that express EGFR and control K562 cells that do not express EGFR were grown in Dulbecco's Modified Eagle Medium (DMEM) containing 10% (v/v) fetal bovine serum to 70-80% confluence in 150 mm petri dishes as described in the Example 1.2. Following the growth, the cells were starved overnight by incubating in the same media except for a reduced concentration of fetal bovine serum—5% (v/v). The cells were washed with cold D-PBS (Dulbecco's Phosphate Buffered Saline, GIBCO #14040-133) and added, in D-PBS, into the wells of plasma treated Multi-Array 96-well plates (Meso Scale Discovery) to yield a range of concentrations from 100 to 5000 cells/well in 25 μL volume. The plates were incubated for 30 min at room temperature to allow the cells to adsorb to the electrode and were then used in an STAG-EGF binding assay.

Example 1.4

Electrochemiluminescence Assay for Binding of STAG-EGF to Immobilized EGFR

To each well having passively adsorbed membrane fragments or whole cells (prepared as described in Examples 1.3.1) was added 25 μL (a sufficient volume to cover the entire bottom of the well) of a solution containing varying concentrations STAG-EGF in PBS containing 3% BSA (as a blocking agent to prevent non-specific binding). The binding reaction was allowed to proceed for 1 h at room temperature. The wells were washed 4 times with PBS and then filled with 150 uL of a solution containing 150 mM tripropylamine (TPA) in phosphate buffer, pH 7.5. Alternatively, in other wells, the wash step was omitted and the TPA solution was added without first removing unbound STAG-EGF ("unwashed assay"). ECL from STAG-EGF bound to immobilized EGFR was then induced and measured using a Sector HTS plate reader (Meso Scale Discovery LLC, Gaithersburg Md.). In the washed assay, it was preferred that the ECL measurement be conducted within a short time period after the addition of the TPA solution (within ~5 min.) to avoid loss of signal due to dissociation of the STAG-EGF. In the unwashed assay, the timing was less important because free ligand remained in solution and the effect of the addition of TPA on the binding equilibrium was small; ECL measurements could be conducted as long as 1 hr after addition of the TPA solution with only small changes in signal. STAG-EGF binding assays using cells and membrane fragments immobilized according to the procedures described in Examples 1.3.2-1.3.5 were carried out using minor variations on the protocol described above.

FIGS. 3A and 3B show the measured ECL signal as a function of the concentration of STAG-EGF for plates having passively adsorbed membrane fragments. FIG. 3A shows results for the assay having a wash step to remove unbound STAG-EGF (washed assay) and FIG. 3B shows results for the assay conducted without removing unbound STAG-EGF (unwashed assay) that takes advantage of the surface selectivity of the ECL measurement for labels on the surface of the electrode as opposed to labels in solution. FIG. 3A shows that STAG-EGF binds specifically to electrodes coated with the EGFR-containing A-431 membranes and that STAG-EGF shows almost no detectable non-specific binding to electrodes coated with the EGFR-free K-562 membranes. FIG. 3B shows that specific binding to A-431 membranes can be observed in binding assays that do not include a wash step (the observed linear increase in signal with [STAG-EGF] over electrodes coated with K-562 membrane fragments is not due to non-specific binding but is due to electrochemiluminescence from STAG-EGF in solution but near the electrode).

Figure 5:
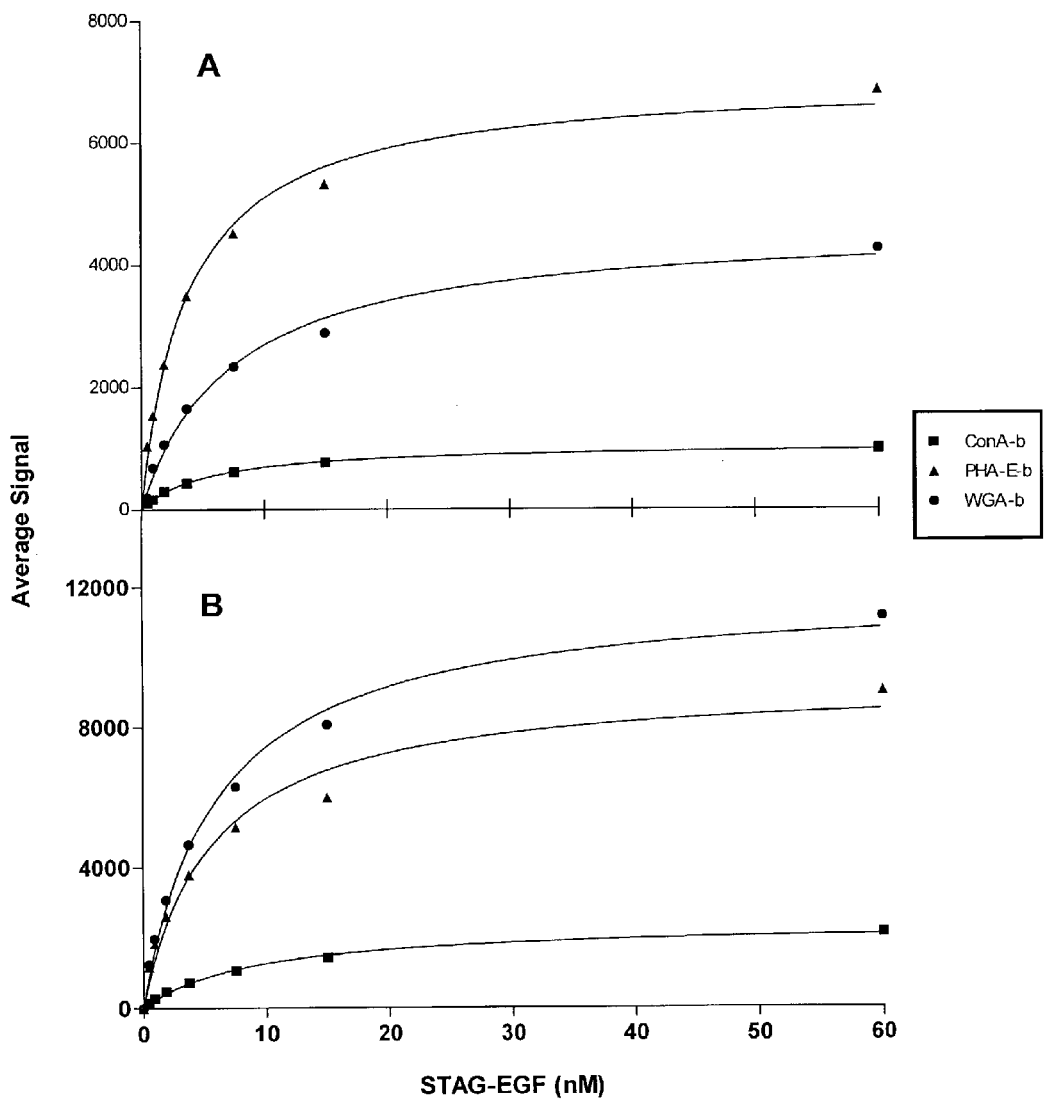
FIG. 5A shows the results of an electrochemiluminescence assay for binding of STAG-EGF to EGFR where the capture of EGFR containing membranes was mediated by lectins passively adsorbed on the electrode surface. The plot shows average ECL signal (vertical axis) as a function of the concentration of STAG-EGF (nM) (horizontal axis).
FIG. 5B shows the results of an electrochemiluminescence assay for binding of STAG-EGF to EGFR where the capture of EGFR containing membranes was mediated by biotinylated lectins preadsorbed on the avidin-coated electrode surface. The plot shows average ECL signal (vertical axis) as a function of the concentration of STAG-EGF (nM) (horizontal axis).

Signals due to non-specific binding and from labels in solution can be corrected for by subtracting the signals observed in the presence of the control cell membranes from that observed in the presence of the EGFR-containing membranes. FIGS. 3C and 3D show the corrected signals as a function of [STAG-EGF] for the washed assay (3C) and the unwashed assay (3D). Both sets of data can be fit to a model assuming a one to one binding interaction having a dissociation constant ($K_d$). The $K_d$ values obtained from FIGS. 3C and 3D, 5 nM and 8 nM respectively, are slightly higher but consistent with literature values (1-4 nM).

FIG. 5A shows the measured baseline-corrected ECL signal as a function of the concentration of STAG-EGF when the EGFR containing membranes were captured using lectins (PHA-E, ConA and WGA) passively immobilized on the surface of a carbon ink electrode. FIG. 5B shows the measured baseline-corrected ECL signal as a function of the concentration of STAG-EGF when the EGFR containing membranes were captured using biotinylated lectins immobilized on the surface of a carbon ink electrode coated with avidin. In these examples, the tripropylamine solution that was added to the wells prior to the ECL measurement was Surfactant Free MSD Assay Buffer G (Meso Scale Discovery). FIG. 6A shows the measured baseline-corrected ECL signal as a function of the concentration of STAG-EGF when the EGFR containing membranes were immobilized using biotinylated anti-EGFR antibodies immobilized on the avidin coated surface of a carbon ink electrode. The method may be especially useful for measurements in a diverse vesicle population when the initial subfractionation by binding properties will be advantageous.

FIG. 6B shows the measured baseline-corrected ECL signal as a function of the concentration of STAG-EGF when whole cells were immobilized on the carbon ink electrodes. In this example, the tripropylamine solution that was added to the wells prior to the ECL measurement was Surfactant Free MSD Assay Buffer G (Meso Scale Discovery).

The insert in the FIG. 6B shows the measured baseline-corrected ECL signal as a function of the number of cell immobilized on the electrode surface when the concentration of STAG-EGF was fixed at 1 nM. The insert figure demonstrates the wide applicability of the method for a broad range of cell concentrations.

Example 1.5

Figure 3:
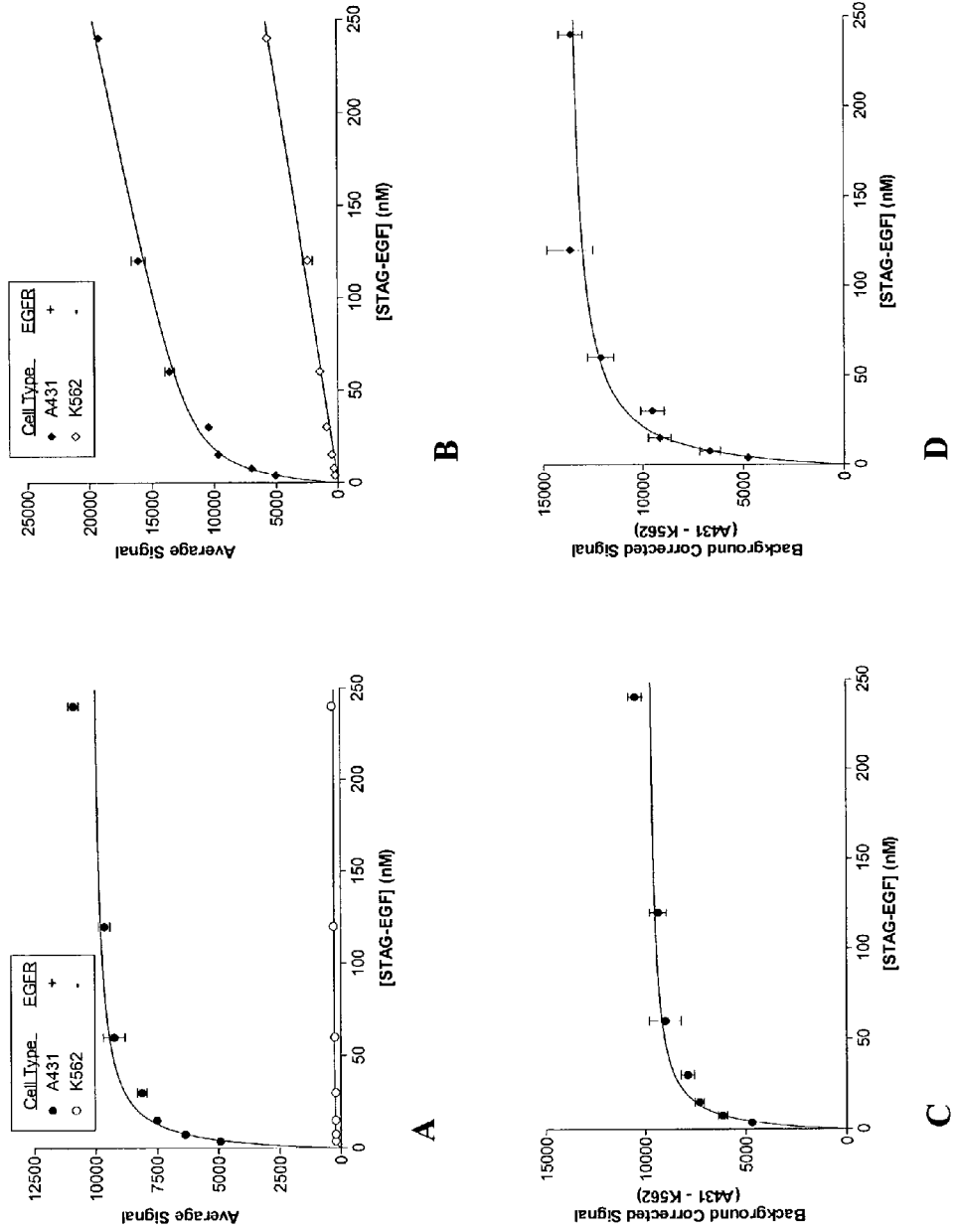
FIG. 3A shows the results of an electrochemiluminescence assay for binding of STAG-EGF to EGFR in passively immobilized membrane fragments. The plot shows average ECL signal (vertical axis) as a function of the concentration of STAG-EGF (nM) (horizontal axis).
FIG. 3B shows the results of an electrochemiluminescence assay for binding of STAG-EGF to EGFR in passively immobilized membrane fragments. The plot shows average ECL signal (vertical axis) as a function of the concentration of STAG-EGF (nM) (horizontal axis).
FIG. 3C shows the results of an electrochemiluminescence assay for binding of STAG-EGF to immobilized EGFR where the plot shows background corrected ECL signal (vertical axis) as a function of the concentration of STAG-EGF (nM) (horizontal axis).
FIG. 3D shows the results of an electrochemiluminescence assay for binding of STAG-EGF to immobilized EGFR in passively immobilized membrane fragments. The plot shows background corrected ECL signal (vertical axis) as a function of the concentration of STAG-EGF (nM) (horizontal axis).
Figure 4:
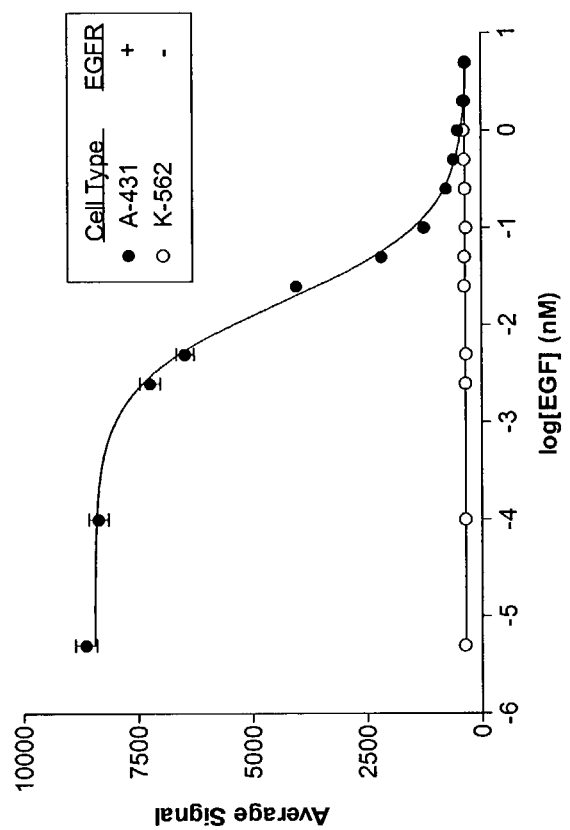
FIG. 4 shows the results of an electrochemiluminescence assay for inhibitors of the binding of STAG-EGF to immobilized EGFR in passively immobilized membrane fragments. The plot shows average ECL signal (vertical axis) as a function of the log concentration of unlabelled EGF (nM) (horizontal axis).

Electrochemiluminescence Assay for Inhibitors of the Binding of STAG-EGF to Immobilized EGFR The EGF-EGFR binding assay may be used to screen for inhibitors of the binding interaction and/or to measure inhibition constants. FIG. 4 shows the inhibition of the binding of STAG-EGF to EGFR by the addition of unlabeled EGF. The experiment was carried out as described in Example 1.4 except that the STAG-EGF (held constant at a concentration of 120 nM) was combined with varying concentrations of unlabeled EGF prior to addition to the wells of the multi-well plate. FIG. 3 shows that EGF effectively competed with STAG-EGF for binding to EGFR and that at the higher concentrations of EGF, inhibition was almost complete (i.e., the signal approached the signal observed with the control cells).

In high throughput screening applications, it is advantageous that the signal in the absence of inhibition is easily and confidently distinguishable from the signal observed in the presence of a strong inhibitor or the background signal observed in the absence of one of the binding partners. The signal to background ratios (calculated as the ratio of the signals obtained from A-431 membranes and K-562 membranes in the presence of 15 nM STAG-EGF) were 34 and 19 for the washed and unwashed assays, respectively. The Z-factors (defined as $1-[(3\sigma_S+3\sigma_B)/(S-B)]$, where $\sigma_S$ and $\sigma_B$ are the standard deviations in the signal and background) for the assays under the same conditions were 0.88 and 0.7, respectively, indicating that the assays are highly suitable for screening applications (see, *J. of Biomolecular Screening*, 1999, 4(2), 67-73).

Example 2

NDP-α-MSH-MC5 Receptor Binding Assay

This Example shows an electrochemiluminescence-based assay measuring the binding of [Nle4,D-Phe7]-α-melanocyte-stimulating hormone (NDP-MSH), an analog of α-melanocyte-stimulating hormone, to immobilized membrane fragments containing the melanocortin 5 receptor (MC5). The melanocortin 5 receptor (MC5) is a seven-transmembrane G-protein-coupled receptor whose natural ligands include melanocortin peptides, adrenocortincotropic hormone and three isoforms of the melanocyte-stimulating hormone (including α-MSH). Besides well documented α-MSH effects such as adrenal cortical steroidogenesis and pigmentation, melanocortin have been also implicated in a number of biological processes including learning and memory, blood pressure control, immune modulation, weight homeostasis and bacterial defense. The key role of the receptor in a number of biological processes makes it a valuable target for drug development efforts. The example is also valuable because MC5 is a representative example of a G-protein-coupled receptor superfamily, and the example demonstrates that the methods of the instant invention can be readily used for high throughput screening involving any member of the superfamily.

The α-MSH-MC5 binding assay uses MC5-containing membrane fragments that are either (i) passively adsorbed on an electrode surface, or (ii) absorbed on the surface of the lectin-coated carbon ink electrode, or (iii) on the avidin coated electrode having preadsorbed biotinylated lectin. While the MC5 receptor is structurally and functionally different from EGFR, the binding of labeled A-MSH to the immobilized MC5 is measured through electrochemiluminescence detection of an electrochemiluminescent label linked to the α-MSH in a manner similar to the binding measurement for the STAG-EGF-EGFR system described above in Example 1. The example demonstrates the surprisingly high versatility and broad applicability of the invention. Furthermore, the ability to measure binding to immobilized membrane fragments (including fragments that are passively adsorbed on a carbon ink electrode surface) is surprising since α-MSH binding to MC5 involves a conformational transition in the receptor and the binding is generally expected to be affected by membrane immobilization, e.g. by changes in membrane fluidity that may occur upon immobilization.

Example 2.1

Labeling of NDP-α-MSH

Synthetic NDP-α-MSH ligand (New England Peptide) was labeled with a Sulfo-TAG and purified by gel filtration chromatography. The product, hereafter referred to as NDP-α-MSH-TAG, had approximately one label per protein molecule.

Example 2.2

Membrane Preparation

The MC5 containing membrane fragments were purchased from Perkin Elmer Life Sciences and used without further purification. The membrane fragments came from HEK-293 cells that were transformed to express MC5. Cell membranes from wild type HEK-293 cells (and that did not express MC5) were also purchased and used as controls.

Example 2.3.1

Direct Immobilization of Membrane Fragments on Carbon Ink Electrodes

Membrane fragments were immobilized by passive adsorption on the screen-printed carbon ink working electrodes of plasma treated Multi-Array 384-well plates. Unless otherwise indicated, the membranes were adsorbed from 5 µL of a 0.15 µg/µL suspension of membranes in Binding Buffer, a buffer containing 25 mM HEPES-KOH, 1.5 mM CaCl2, 1 mM MgSO4, 100 mM NaCl, and protease inhibitors. Plates were sealed and incubated for 1 h at ambient temperature. Following the incubation, wells were blocked with 20 µL of a blocking solution consisting of 0.01% polyethyleneimine (PEI) and 3% BSA in Binding Buffer. Plates were sealed and incubated for 30 min at ambient temperature. The liquid in the wells was discarded and the plates used for NDP-α-MSH-TAG binding assay.

Example 2.3.2

Immobilization of Membrane Fragments Utilizing Lectins Directly Preadsorbed on Carbon Ink Electrodes Pure PHA-E was passively adsorbed onto the working electrode of plasma-treated Multi-Array 384-well plates by dispensing PHA-E (10 pmol per well) in PBS (5 µL per well) into the wells of the plate. Plates were sealed and incubated for 1 h at ambient temperature. Following the incubation, 3% BSA blocking solution was added (65 µL per well) and the plates were sealed and incubated for 1 h at room temperature.

Plates were washed 4 times with PBS and dried. MC5 containing membrane fragments were immobilized in the plates using the procedure described in Example 2.3.1 except that in this case the immobilization occurred via lectin-sugar interactions.

Example 2.3.3

Improved Immobilization of Membrane Fragments Utilizing Biotinylated Lectins Preadsorbed on Avidin-Coated Carbon Ink Electrodes Plasma-treated Multi-Array plates having avidin-coated working electrodes were further coated with biotinylated PHA-E using the procedure described in Example 2.3.2 except that the immobilization occurred via biotin-avidin interaction. MC5 containing membrane fragments were immobilized in the plates using the procedure described in the Example 2.3.1.

Example 2.4

Electrochemiluminescence Assay for Binding of NDP-α-MSH-TAG to Immobilized MC5

The binding assay was performed by adding 10 μL of a solution containing NDP-α-MSG-TAG (in Binding Buffer plus 3% BSA) to the wells of plates containing immobilized MC5 containing membranes. The binding reaction was allowed to proceed for 1 hr at ambient temperature. The fluid in the wells was then removed and 35 μL of a buffered detergent-free solution of tripropylamine (MSD Assay Buffer T, surfactant free, Meso Scale Discovery) was added. ECL from the wells was measured using a Sector HTS plate reader.

FIG. 7A shows the measured baseline-corrected ECL signal as a function of the concentration of NDP-α-MSH-TAG when the MC5 containing membranes were passively immobilized on the carbon ink electrode as described in Example 2.3.1. FIGS. 7B and C show the measured ECL signal as a function of the concentration of NDP-α-MSH-TAG when the MC5 containing membranes were immobilized via capture on (B) passively adsorbed lectins as described in Example 2.3.2 or (C) lectins that were immobilized through biotin-avidin interactions as described in Example 2.3.3. Each of the immobilization conditions were useful for immobilizing functional MC5 and for detecting binding to the MC5 via an electrochemiluminescence measurement.

The inserts in FIGS. 7A-C show the measured baseline-corrected ECL signal as a function of the concentration of the immobilized membrane when the concentration of NDP-α-MSH-TAG was fixed at 1.0 nM. The inserts demonstrate the applicability of the method for a wide range of membrane concentrations.

Example 2.5

Electrochemiluminescence Assay for Inhibitors of the Binding of NDP-α-MSH-TAG to Immobilized MC5

The binding assay may be used to screen for inhibitors of the binding interaction and/or to measure inhibition constants. FIG. 8 shows the inhibition of the binding of NDP-α-MSH-TAG to MC5 by the addition of unlabeled NDP-α-MSH. In this Example, MC5 containing membrane fragments were immobilized on the electrode surface of plasma treated Multi-Array 96 well plates (Meso Scale Discovery) by capture on a passively adsorbed layer of pure Pokeweed Mitogen according to an immobilization protocol analogous to that described in the Example 2.3.2. The inhibition assay was carried out by adding 25 μL of a solution containing a mixture of unlabeled NDP-α-MSH and 120 nM NDP-α-MSH-TAG in Binding Buffer plus 3% BSA and incubating for 1 hr at ambient temperature. The fluid in the wells was then removed and 150 μL of a buffered detergent-free solution of tripropylamine (MSD Assay Buffer T, surfactant free, Meso Scale Discovery) was added. ECL from the wells was measured using a Sector HTS plate reader.

FIG. 8 shows that NDP-α-MSH effectively competed with NDP-α-MSH-TAG for binding to MC5 with a binding constant ($EC_{50}$) equal to 3.2 nM and that at the higher concentrations of NDP-α-MSH-TAG, inhibition was almost complete (i.e., the signal approached the signal observed with the control cells that did not express MC5).

Example 3

Measuring of EGFR Activation Dependent Phosphorylation (Prophetic)

A431 cells are exposed to EGF so as to activate the EGFR. Activation of EGFR leads to its autophosphorylation. The cells are lysed as described in Example 1.2 to form cell membrane fragments (and, preferably, purified by centrifugation). The cell membrane fragments are immobilized on carbon electrodes integrated into the multi-well plates by passive adsorption or specific binding to a capture reagent previously immobilized on the electrode (e.g., wheat germ agglutinin, anti-EGFR, or another antibody specific for a membrane component, preferably, an epitope found on the cytoplasmic side) (as described in Example 1.3). The immobilized membrane fragments are treated with a buffered solution containing a STAG-labeled anti-phosphotyrosine antibody. In an alternate protocol, the membranes and antibody are premixed prior to addition of the membranes to the wells. A buffered tripropylamine solution is introduced to the well and ECL is induced and measured as described in Example 1.4. The ECL signal measured for EGF-activated cells is greater than that measured for control A431 cells that were not exposed to EGF, indicating that EGF activation results in phosphorylation of membrane components.

Example 4

Measurement of EGFR Activation Dependent Binding Events (Prophetic)

A431 cells are exposed to EGF so as to activate the EGFR. Activation of the EGFR leads to autophosphorylation of EGFR followed by the sequential binding of shc to EGFR and grb-2 to shc. The cells are lysed as described in Example 1.2 to form cell membrane fragments (and, preferably, purified by centrifugation). The cell membrane fragments are immobilized on carbon electrodes integrated into the multi-well plates by passive adsorption (as described in Example 1.3) or specific binding to a capture reagent immobilized on the electrode (e.g., wheat germ agglutinin, anti-EGFR, or another antibody specific for a membrane component, preferably, an epitope found on the cytoplasmic side). The immobilized membrane fragments are treated with a buffered solution containing an STAG-labeled antibody directed against shc or grb-1. In an alternate protocol, the membranes and antibody are premixed prior to addition of the membranes to the wells. A buffered tripropylamine solution is introduced into the well and ECL is induced and measured as described in Example 1.4. The ECL signal measured for EGF-activated cells is greater than that measured for control A431 cells that were not exposed to EGF, indicating that EGF activation results in the sequestration of the soluble proteins shc and grb-1 to the cell membrane.

Example 5

Measurement of VEGF-VEGFR Binding Interaction with Recombinant Cell Lines (Prophetic)

This example illustrates the use of the electrodes and technique of the invention to measure the activity of a recombinant membrane protein that is expressed or over-expressed in a cell line that does not normally express the protein (or expresses very low levels). The vascular endothelial growth factor receptor (VEGFR) is expressed (preferably, stably), according to methods known in the art (e.g., by introducing the VEGFR gene in an appropriate plasmid vector), in a suitable cell line that does not normally express VEGFR (e.g., HEK-293 cells, a cell line that is available from the American Type Culture Collection, Manassas, Va.). Clones of HEK-293 cells containing the vector are selected by virtue of the presence of a selectable genetic marker on the plasmid. The clones are characterized for the abundance of VEGFR by standard western blot analysis and individual lines are selected for further study that express at least $10^3$ receptors per cell, more preferably at least $10^4$ receptors per cell, more preferably at least $10^5$ receptors per cell and most preferably $10^6$ receptors per cell.

The activity of the VEGFR in the engineered clonal cell lines is confirmed by examining the autophosphorylation of VEGFR in the engineered cells in response to challenge with the cognate ligand, vascular endothelial growth factor (VEGF). Those skilled in the art will appreciate that functional receptors in the cell lines will undergo auto-transphosphorylation in response to VEGF that can be monitored through immunoprecipitation of the VEGFR from the cells and subsequent analysis by western blot with an anti-phosphotyrosine antibody. A cell line is selected that contains preferably at least $10^4$ functional receptors per cell, more preferably at least $10^5$ functional receptors per cell and most preferably $10^6$ functional receptors per cell.

Membranes fragments are prepared from the engineered cell line and from the parental HEK-293 cells line as described in Example 1.2. A labeled form of VEGF (STAG-VEGF) is prepared as described in Example 1.1. Membranes from the engineered cell line over-expressing VEGFR are immobilized on carbon electrodes as in Example 1.3. In a separate experiment, membranes from wild type HEK-293 cells are immobilized on carbon electrodes for use as negative controls. An electrochemiluminescence assay for binding of STAG-VEGF to immobilized VEGFR is conducted as in Example 1. An electrochemiluminescence assay for inhibitors of the binding of STAG-VEGF to immobilized VEGFR is conducted as described in Example 1.5. Measurement of VEGFR activation dependent phosphorylation is conducted as in Example 3. Measurement of VEGFR activation dependent binding events is conducted as in Example 4.

Example 6

Measurement of VEGF-VEGFR Binding Interaction with Recombinant, Purified Receptor (Prophetic)

Recombinant, purified VEGFR is commercially available (e.g. R&D Systems, Inc.) in several forms. In one form, the recombinant purified receptor constitutes the extracellular, VEGF binding domain of the receptor fused to the Fc domain of an IgG human antibody. The Fc domain is a target for binding by anti-species antibodies (e.g., a rabbit anti-human antibody). Biotinylated, anti-human Fc antibody is immobilized by adding 0.5 µg of the antibody (in 5 ul PBS) to a well of a 96-well plate containing a carbon electrode coated with streptavidin and incubating for 30 min at ambient temperature. The wells are blocked with 200 ul of 3% BSA (bovine serum albumin)/0.05% PEI (poly-ethylene imine) for one hour at ambient temperature. Next, the wells are washed four times with PBS. Then, 0.2 pmol/well of recombinant receptor 25 µl of a 0.5% BSA, buffered solution are added and the plate shaken intermittently for 1 h at ambient temperature. Next, the plates are washed four times with PBS. The STAG-VEGF is added at (50 µL of a 1 nM solution) in a buffered solution containing 3% (w/v) BSA and incubated for 3 hours with intermittent shaking at ambient temperature. The plates are then washed four times with PBS. Finally, 100 µl of a buffered tripropylamine solution is introduced to the well and ECL is induced and measured as described in Example 1.4. An electrochemiluminescence assay for inhibitors of the binding of STAG-VEGF to immobilized recombinant, purified receptor is conducted as described in Example 1.5.

Example 7

Immobilization of α-1-Acidglycoprotein on Lectin-Coated Electrodes

This example shows an electrochemiluminescence-based assay measuring the binding of α-1-acidglycoprotein (AGP) to lectins immobilized on the surface of the carbon electrode. The example demonstrates that a free glycosylated protein (i.e., a protein that is not a component of a biological membrane) can be immobilized on the surface of an electrode.

Lectins were immobilized by passive adsorption onto carbon ink electrodes or by the binding of biotin-labeled lectins onto avidin-coated carbon ink electrodes. The carbon ink working electrodes of plasma treated 384-well Multi-Array plates (Meso Scale Discovery) were coated with PHA-E, ConA or WGA lectins by treating the electrodes with 5 µl of a 2 µM solution of the lectin in PBS. PBS solution with no lectin was used as a background control. The plates were sealed and incubated for an hour at ambient temperature. The plates were blocked by adding 70 µl of a blocking solution (MSD Blocker A, Meso Scale Discovery) and washed with PBS. Biotin-labeled lectins were immobilized using an analogous procedure except that the working electrode of the Multi-Array plates were precoated with avidin.

Serial dilutions of AGP labeled with Sulfo-TAG NHS Ester (STAG-AGP) were prepared in PBS and added to wells of the lectin-coated Multi-Array plates (5 µl per well). Each condition was tested in duplicate. The plate was sealed and incubated for 15 hours at ambient temperature. Following the incubation, 30 µl MSD T assay buffer (Meso Scale Discovery) aliquots were added per well and the plates were analyzed on a Sector HTS instrument.

FIGS. 9A and B show the measured ECL signal as a function of the concentration of TAG-AGP for lectins (ConA, PHA-E and WGA) that were either immobilized directly (A) or through biotin-avidin interactions(B).

Example 8

Immunohistochemistry Using Electrochemiluminescence Detection

The example demonstrates the measurement of tyrosine phosphatase activity and inhibition by measuring the cellular phosphotyrosine content in whole cells grown on a carbon electrode surface. The example demonstrates in principle that a variety of cellular analytes may be detected in cells grown on a carbon electrode surface without undue experimentation. The example also shows that internal cellular components may be measured using electrochemiluminescence detection in whole cells that are fixed and permeabilized on an electrode. The versatility and broad applicability of the method allows detection of any cellular protein, carbohydrate, lipid or small molecule against which an antibody can be directed.

U2-OS cells were grown in non-plasma treated Multi-Array plates using the growth conditions recommended by the American Type Culture Collection (ATCC reference number HTB-96). The plates were partially sterilized beforehand by illumination with a high energy UV light (Strata Linker Model 2400, Stratagene) set to deliver 9999 joules to the plate surface over the course of 5 minutes. Approximately 10,000 trypsinized cells were dispensed to each well of the 96 well plate in 100 µl of tissue culture media (see ATCC reference above) and incubated overnight in a cell culture incubator (at 37° C. in a humidified atmosphere containing 5% $CO_2$) to promote attachment of the cells to the electrode surface.

Per-Vanadate, a tyrosine phosphatase inhibitor was added to a some of the wells to give a final concentration of 1 mM in those wells. Per-Vanadate treatment is documented to raise intracellular phosphotyrosine content (Lund-Johansen F, Frey T, Ledbetter J A, and Thompson P A, Cytometry. Oct. 1, 1996; 25(2):182-90). Some wells were left untreated as negative controls. Following a 30 minute incubation in the cell culture incubator, the media was removed and the cells were fixed with ice cold 99% Isopropanol for 10 minutes. The wells were washed once in phosphate buffered saline (PBS) containing 10% Fetal Bovine Serum (PBS/FBS) and blocked in 100 µl of the same media for an additional one hour.

Phosphotyrosine containing proteins were detected by incubating the wells for one hour in 90 µl of PBS/FBS containing an anti-phosphotyrosine monoclonal antibody (100 ng/mL) and an anti-mouse secondary antibody (200 ng/mL) that was labeled with ruthenium-tris-bipyridine (ORI-TAG NHS Ester, IGEN International). In some wells, the anti-phosphotyrosine antibody was replaced with an antibody that was not expected to bind any component of the sample; these wells were used to measure the assay background signal. The plates were incubated at ambient temperature for one hour then washed three times with PBS. ECL Assay Buffer was added (150 µl of OriGlo Plus, IGEN International) and the plate was analyzed using a Sector HTS instrument.

TABLE 1

| Treatment | No Addition | Background | Per-vanadate |
|---|---|---|---|
| Average | 1997.4 | 278.0 | 7690.0 |
| Standard dev. | 218.0 | 8.0 | 922.0 |

Table 1 shows that the cells treated with Per-Vanadate gave ECL signals (after subtraction of background) that were more than three times higher than the untreated cells. In all cases the number of samples n=4. Averages and standard deviations for these four wells are shown in the Table. As a further specificity control cells were treated with per-vanadate and detection was using an isotype control antibody instead of the anti-phosphotyrosine antibody PY20. This is represented in the column "background". The results were consistent with the expected change in cellular phosphotyrosine content and show that ECL assays on fixed cells can be used to measure internal components of the cells. Furthermore data demonstrate that the basal level of phosphotyrosine in a cell can be measured using an isotype control antibody which demonstrates the level of sensitivity achieved in the instant invention.

Example 9

EGF—EGFR Binding Assays Using EGFR Containing Membranes Immobilized on Magnetizable Particles Streptavidin-coated magnetizable beads having a diameter of 2.8 µm (Streptavidin ORI-BEADS, IGEN International) were coated with biotinylated WGA by incubating the beads in a solution of biotinylated WGA in a phosphate buffered saline containing BSA as a blocking agent (ORI-BEAD Binding Buffer, IGEN International). The beads were washed with ORI-BEAD Binding Buffer in a magnetic separator and diluted in ORI-BEAD Binding Buffer to a concentration of 1 mg/mL.

A-431 and control K562 membranes, prepared as described in the Example 1.2, were diluted into ORI-BEAD Binding Buffer to a concentration of 0.1 µg/µl. Equal volumes of dilute WGA coated beads and dilute membranes were mixed and incubated at ambient temperature with constant shaking for two hours. The membrane-coated beads were then washed ORI-BEAD Binding Buffer in a magnetic separator and diluted in ORI-BEAD Binding Buffer to a concentration of 0.1 mg of beads per mL.

The membrane-coated beads (100 µL) were transferred into round bottom polypropylene 96-well plates and combined with 100 µL of solutions containing varying amounts of STAG-EGF. The plates were incubated for 60 min. at room temperature and then analyzed on an M-Series M-8 Analyzer (IGEN International). Measurements on the M-8 instrument involve aspirating the beads into a flow cell that comprises a platinum electrode. A magnet in the instrument pulls the beads onto the surface of the electrode. The beads are washed with a buffered solution containing tripropylamine and a surfactant (ORI-GLOW Plus, IGEN International) and ECL is induced by applying a potential to the electrode. FIG. 10 shows the ECL signal due to the binding of TAG-EGF to the EGFR (plotted as the difference in signals between measured using the A-431 and negative control K562 membranes). Surprisingly, reasonable ECL signals were observed despite the presence of surfactant in the tripropylamine solution.

The insert of FIG. 10 shows the ration of a measured ECL signal to a background signal as a function of STAG-EGF concentration therefore defining the optimal and useful ranges of substrate use.

7. INCORPORATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A method of measuring an analyte in a lipid/protein layer, said method comprising:
   (a) providing an electrode having a lipid/protein layer immobilized thereon, wherein said lipid/protein layer is comprised in or derived from whole cells, organelles, tissues, membrane fragments, liposomes, membrane ghosts, cell membranes, organelle membrane fragments, organelle membranes, virions, virion membrane fragments, virion membranes, liposomes, and combinations thereof;

(b) permeabilizing said lipid/protein layer;

(c) contacting said electrode with a solution comprising a binding partner of said analyte, said binding partner being labeled with an electrochemiluminescent label;

(d) forming a complex comprising said analyte and said binding partner; and (e) measuring said complex using electrode induced luminescence.

2. The method of claim 1, wherein said permeabilization step forms a stable tissue layer on said electrode.

3. The method of claim 1, wherein said analyte comprises an internal cellular component.

4. The method of claim 1, wherein said electrode induced luminescence is induced by applying electrical energy to said one or more electrodes.

5. The method of claim 1, wherein said electrode induced luminescence is induced in the presence of a solution comprising an electrochemiluminescence coreactant.

6. The method of claim 5, wherein said coreactant is a trialkylamine.

7. The method of claim 5, wherein said solution does not comprise a surfactant.

8. The method of claim 5, wherein said solution comprises a surfactant.

9. The method of claim 1, wherein said analyte comprises a receptor.

10. The method of claim 9, wherein said receptor is a membrane receptor.

11. The method of claim 10, wherein said receptor is embedded into said lipid/protein layer.

12. The method of claim 9, wherein said receptor remains active upon immobilization of said lipid/protein layer on said electrode.

13. The method of claim 9, wherein said receptor is selected from a group consisting of transmembrane receptors with intrinsic tyrosine kinase activity, non-tyrosine kinase transmembrane receptors, G-protein coupled receptors, GPCR effector proteins, organelle-bound GTPases, guanine nucleotide exchange factors, GTPase activating proteins, cytokine/chemokine receptors, cell adhesion molecules, cytoplasmic peripheral membrane protein kinases, intracellular protein kinase adaptor/docking proteins, ion channels, passive transporter proteins, active ATP-driven transporters, ion-linked transporters, glycosyltranferases and glycoprotein modifying enzymes.

14. The method of claim 1, wherein said lipid/protein layer is immobilized on said electrode via pokeweed mitogen.

15. The method of claim 1, wherein a plurality of lipid/protein layers are immobilized on said electrode in the form of an array and at least two of the lipid/protein layers differ in composition and/or biological source.

16. The method of claim 15, wherein said lipid/protein layer is comprised in or derived from a substance selected from virions, tissues, liposomes, membrane ghosts or combinations thereof.

17. The method of claim 16, wherein said analyte is a receptor and said binding partner comprises a ligand of said receptor.

18. The method of claim 1, wherein said lipid/protein layer is comprised in or derived from membrane fragments.

19. The method of claim 14, wherein said pokeweed mitogen has a protein/carbohydrate ratio greater than or equal to 1.0.

20. The method of claim 19, wherein said pokeweed mitogen has a protein/carbohydrate ratio greater than or equal to 2.5.

21. The method of claim 14, wherein said pokeweed mitogen has a protein/carbohydrate ratio greater than or equal to 9.

22. The method of claim 1, wherein said electrode is a screen-printed electrode.

23. The method of claim 1, wherein said electrode is treated to enhance the adsorptive properties of said electrode.

24. The method of claim 23, wherein said carbon ink electrode is plasma-treated.

25. The method of claim 1 wherein said electrode comprises a spacer layer between said electrode and said lipid/protein layer, wherein said spacer layer occupies a hydrophilic spacer volume.

26. The method of claim 1 wherein said lipid/protein layer retain at least 20% of its biological activity after immobilization to said electrode.

27. The method of claim 1 wherein said lipid/protein layer retain at least 30% of its biological activity after immobilization to said electrode.

28. The method of claim 1 wherein said lipid/protein layer retain at least 40% of its biological activity after immobilization to said electrode.

29. The method of claim 1 wherein said lipid/protein layer retain at least 50% of its biological activity after immobilization to said electrode.

30. The method of claim 1 wherein lipid/protein layer is immobilized on said electrode via lectin.

31. A method of measuring a plurality of analytes in a lipid/protein layer, wherein said plurality of analytes comprises internal cellular components, external cellular components, or combinations thereof, said method comprising:

(f) providing an electrode having a lipid/protein layer immobilized thereon, wherein said lipid/protein layer is comprised in or derived from whole cells, organelles, tissues, membrane fragments, liposomes, membrane ghosts, cell membranes, organelle membrane fragments, organelle membranes, virions, virion membrane fragments, virion membranes, liposomes, and combinations thereof;

(g) permeabilizing said lipid/protein layer;

(h) contacting said electrode with a solution comprising a plurality of binding partners of said plurality of analytes, wherein said plurality of binding partners are labeled with an electrochemiluminescent label;

(i) forming a plurality of complexes each comprising an analyte bound to a binding partner of said cellular component; and (j) measuring said plurality of complexes using electrode induced luminescence.

32. The method of claim 31 wherein said plurality of analytes comprises a combination of internal and external cellular components.

33. The method of claim 31, wherein said electrode induced luminescence is induced by applying electrical energy to said one or more electrodes.

34. The method of claim 31, wherein said electrode induced luminescence is induced in the presence of a solution comprising an electrochemiluminescence coreactant.

35. The method of claim 34, wherein said coreactant is a trialkylamine.

36. The method of claim 34, wherein said solution does not comprise a surfactant.

37. The method of claim 34, wherein said solution comprises a surfactant.

38. The method of claim 31, wherein said plurality of analytes comprises a receptor.

39. The method of claim 38, wherein said receptor is a membrane receptor.

40. The method of claim 39, wherein said receptor is embedded into said lipid/protein layer.

41. The method of claim 39, wherein said receptor remains active upon immobilization of said lipid/protein layer on said electrode.

42. The method of claim 38, wherein said receptor is selected from a group consisting of transmembrane receptors with intrinsic tyrosine kinase activity, non-tyrosine kinase transmembrane receptors, G-protein coupled receptors, GPCR effector proteins, organelle-bound GTPases, guanine nucleotide exchange factors, GTPase activating proteins, cytokine/chemokine receptors, cell adhesion molecules, cytoplasmic peripheral membrane protein kinases, intracellular protein kinase adaptor/docking proteins, ion channels, passive transporter proteins, active ATP-driven transporters, ion-linked transporters, glycosyltranferases and glycoprotein modifying enzymes.

43. The method of claim 31, wherein a plurality of lipid/protein layers are immobilized on said electrode in the form of an array and at least two of the lipid/protein layers differ in composition and/or biological source.

44. The method of claim 31, wherein said permeabilization step forms a stable tissue layer on said electrode.

45. The method of claim 31, wherein said electrode is a screen-printed electrode.

46. The method of claim 31, wherein said electrode is treated to enhance the adsorptive properties of said electrode.

47. The method of claim 46, wherein said electrode is plasma-treated.

48. The method of claim 31, wherein said electrode comprises a spacer layer between said electrode and said lipid/protein layer, wherein said spacer layer occupies a hydrophilic spacer volume.

49. The method of claim 31, wherein said lipid/protein layer retains at least 20% of its biological activity after immobilization to said electrode.

50. The method of claim 31, wherein said lipid/protein layer retains at least 30% of its biological activity after immobilization to said electrode.

51. The method of claim 31, wherein said lipid/protein layer retains at least 40% of its biological activity after immobilization to said electrode.

52. The method of claim 31, wherein said lipid/protein layer retains at least 50% of its biological activity after immobilization to said electrode.

53. The method of claim 31 wherein said lipid/protein layer is immobilized on said electrode via lectin or pokeweed mitogen.

* * * * *